United States Patent
Soletti et al.

(10) Patent No.: US 9,867,690 B2
(45) Date of Patent: Jan. 16, 2018

(54) SYSTEM AND MANDREL FOR CREATING GRAFT DEVICES

(75) Inventors: Lorenzo Soletti, Pittsburgh, PA (US); Mohammed S. El-Kurdi, Pittsburgh, PA (US); Jon McGrath, Duxbury, MA (US); J. Christopher Flaherty, Topsfield, MA (US); Liem Vu, Needham, MA (US); Jerry Brightbill, Newton, MA (US); Stephen Evans, Westford, MA (US); Joseph Ting, Framingham, MA (US); David Rezac, Westborough, MA (US); Timothy Robinson, Sandown, NH (US)

(73) Assignee: NEOGRAFT TECHNOLOGIES, INC., Taunton, MA (US)

( * ) Notice: Subject to any disclaimer, the term of this patent is extended or adjusted under 35 U.S.C. 154(b) by 760 days.

(21) Appl. No.: 13/984,249

(22) PCT Filed: Feb. 8, 2012

(86) PCT No.: PCT/US2012/024251
§ 371 (c)(1),
(2), (4) Date: Nov. 14, 2013

(87) PCT Pub. No.: WO2012/109309
PCT Pub. Date: Aug. 16, 2012

(65) Prior Publication Data
US 2014/0058194 A1    Feb. 27, 2014

Related U.S. Application Data

(60) Provisional application No. 61/441,078, filed on Feb. 9, 2011.

(51) Int. Cl.
*A61F 2/04* (2013.01)
*A61F 2/06* (2013.01)
(Continued)

(52) U.S. Cl.
CPC .......... *A61F 2/062* (2013.01); *B05B 13/0436* (2013.01); *B05B 13/0627* (2013.01);
(Continued)

(58) Field of Classification Search
CPC ...................................................... A61F 2/062
See application file for complete search history.

(56) References Cited

U.S. PATENT DOCUMENTS

| 4,323,525 A | 4/1982 | Bornat |
| 4,475,972 A | 10/1984 | Wong |

(Continued)

FOREIGN PATENT DOCUMENTS

JP    H 1176278 A    3/1999

OTHER PUBLICATIONS

Ayres, et al. Modulation of anisotropy in electrospun tissue-engineering scaffolds: Analysis of fiber alignment by the fast Fourier transform. Biomaterials 27 (2006) 5524-5534.
(Continued)

*Primary Examiner* — Charles A Marmor, II
*Assistant Examiner* — Thaddeus Cox
(74) *Attorney, Agent, or Firm* — Wilson Sonsini Goodrich & Rosati

(57) ABSTRACT

A system for applying a fiber matrix on a tubular member is provided. A mandrel, configured for atraumatic placement within the tubular member, is included. Methods for atraumatic placement of a mandrel into a tubular member are also provided.

15 Claims, 15 Drawing Sheets

(51) Int. Cl.
B05B 13/00 (2006.01)
B05B 13/04 (2006.01)
B05B 13/06 (2006.01)
A61B 17/00 (2006.01)
(52) U.S. Cl.
CPC .............. *A61B 2017/00526* (2013.01); *A61B 2017/00969* (2013.01); *A61F 2210/0076* (2013.01)

(56) References Cited

U.S. PATENT DOCUMENTS

| | | | |
|---|---|---|---|
| 4,738,740 A | 4/1988 | Pinchuk | |
| 4,798,606 A | 1/1989 | Pinchuk | |
| 4,878,908 A * | 11/1989 | Martin | A61L 15/24 623/1.54 |
| 4,909,979 A * | 3/1990 | Possis | A61F 2/062 264/230 |
| 5,792,603 A * | 8/1998 | Dunkelman | C12M 41/00 435/1.2 |
| 6,016,848 A * | 1/2000 | Egres, Jr. | F16L 9/12 138/109 |
| 6,022,445 A * | 2/2000 | Fofonoff | B29C 37/0017 156/247 |
| 6,030,371 A | 2/2000 | Pursley | |
| 6,254,627 B1 * | 7/2001 | Freidberg | A61F 2/07 606/195 |
| 6,293,998 B1 * | 9/2001 | Dolan | B01D 53/0462 95/106 |
| 6,891,077 B2 | 5/2005 | Rothwell et al. | |
| 7,166,124 B2 | 1/2007 | Xie et al. | |
| 8,124,001 B1 * | 2/2012 | Wen | D01D 5/0076 264/465 |
| 2002/0042128 A1 | 4/2002 | Bowlin et al. | |
| 2002/0188349 A1* | 12/2002 | McAllister | A61F 2/06 623/1.41 |
| 2004/0073294 A1 | 4/2004 | Diaz et al. | |
| 2004/0094873 A1 | 5/2004 | Dubson et al. | |
| 2004/0146546 A1 | 7/2004 | Gravett et al. | |
| 2005/0203636 A1 | 9/2005 | McFetridge | |
| 2006/0240061 A1 | 10/2006 | Atala et al. | |
| 2007/0207186 A1* | 9/2007 | Scanlon | A61F 2/07 424/424 |
| 2007/0215268 A1* | 9/2007 | Pingleton | A61M 25/0009 156/169 |
| 2007/0259102 A1* | 11/2007 | McNiven | B05B 13/0207 427/2.25 |
| 2008/0157444 A1* | 7/2008 | Melsheimer | A61M 25/1027 264/514 |
| 2008/0208323 A1 | 8/2008 | El-Kurdi et al. | |
| 2009/0030580 A1 | 1/2009 | Doi | |
| 2010/0030321 A1* | 2/2010 | Mach | A61F 2/07 623/1.18 |
| 2011/0087070 A1* | 4/2011 | Tilson | A61B 1/00135 600/121 |
| 2011/0144689 A1* | 6/2011 | Isch | A61B 17/12022 606/194 |
| 2012/0330437 A1* | 12/2012 | El-Kurdi | A61F 2/06 623/23.64 |

OTHER PUBLICATIONS

Ben-Gal, et al. Expandable external support device to improve saphenous vein graft patency after CABG. J Cardiothorac Surg 2013;8:122.
Castronuovo, J. The sequence of gene expression in cultured human saphenous vein after injury. (2002) J. Vasc. Surg. 35, 146-151.
Chakrabarty, S. Fibrin solubilizing properties of certain anionic and cationic detergents. Thrombosis research 55.4 (1989): 511-519.
Courtney, et al. Design and analysis of tissue engineering scaffolds that mimic soft tissue mechanical anisotropy. Biomaterials. 2006, 27: 3631-3638.
Deitzel, et al. Controlled deposition of electrospun poly(ethylene oxide) fibers. Polymer. 2001, 42: 8163-8170.
Deitzel, et al. The effect of processing variable on the morphology of electrospun nanofibers and textiles. Polymer 42 (2001): 261-272.
Fingerle. Intimal lesion formation in rat carotid arteries after endothelial denudation in absence of medial injury. (1990) Arteriosclerosis, 10, 1082-1087.
Grote, et al. Mechanical stretch enhances mRNA expression and proenzyme release of matrix metalloproteinase-2 (MMP-2) via NAD(P)H oxidase-derived reactive oxygen species. Circulation Research. 2003;92(11): 80-6.
Hermans, et al. Fibrin: structure and interactions. Seminars in thrombosis and hemostasis. vol. 8. No. 1. 1982.
International search report and written opinion dated Aug. 22, 2012 for PCT Application No. US2012/024251.
Izzat, et al. Influence of external stent size on early medial and neointimal thickening in a pig model of saphenous vein bypass grafting. Circulation 1996; 94:1741-5.
Janowski-Bell, et al. Histology of Blood Vessels—www2.victoriacollege.edu/dept/bio/Belltutorials/Histology%20Tutorial/Blood%20Vessels/Histology_of_Blood_Vessels.html.
Jeremy, et al. A bioabsorbable (polyglactin), nonrestrictive, external sheath inhibits porcine saphenous vein graft thickening. J Thorac Cardiovasc Surg. 2004;127(6): 1766-72.
Kohler, et al. The effect of rigid external support on vein graft adaptation to the arterial circulation. J Vasc Surg. 1989;9(2): 277-85.
Levorson, et al. Fabrication and characterization of multiscale electrospun scaffolds for cartilage regeneration. Biomed Mater 2013;8:014103. doi:10.1088/1748-6041/8/1/014103.
Linder, V. Mouse model of arterial injury. (1993) Circ. Res., 73, 792-796.
Manchio, J. Disruption of graft endothelium correlates with early failure after off-pump coronary artery bypass surgery. (2005) Ann. Thor. Surg. 79, 1991-1998.
McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Mehta, et al. External stenting reduces long-term medial and neointimal thickening and platelet derived growth factor expression in a pig model of arteriovenous bypass grafting. Nat Med. 1998;4(2): 235-9.
Morton, et al. Electrospun fibrin nanofibers for the use in tissue engineering. Modification of fibrin to improve applications in regenerative medicine (2010): 81.
Mosesson, M. W. Fibrinogen and fibrin structure and functions. Journal of Thrombosis and Haemostasis 3.8 (2005): 1894-1904.
Parsonnet, et al. New stent for support of veins in arterial grafts. Arch Surg. 1963;87: 696702.
Perumcherry, et al. A Novel Method for the Fabrication of Fibrin-Based Electrospun Nanofibrous Scaffold for Tissue-Engineering Applications. Tissue Engineering Part C: Methods 17.11 (2011): 1121-1130.
Ramos, et al. Histologic fate and endothelial changes of distended and nondistended vein grafts. Ann Surg. 1976;183(3): 205-28.
Reneker, et al. Electrospinning of Nanofibers from Polymer Solutions and Melts. Adv Appl Mech 2007;41. doi:10.1016/S0065-2156(07)41002-X.
Sell, et al. Cross-linking methods of electrospun fibrinogen scaffolds for tissue engineering applications. Biomedical Materials 3.4 (2008): 045001.
Sepehipour, A. Does a 'no-touch' technique result in better vein patency? (2011) Interact Cardiovasc Thorac Surg., 13, 626-630.
Sreerekha, et al. Fabrication of fibrin based electrospun multiscale composite scaffold for tissue engineering applications. Journal of biomedical nanotechnology 9.5 (2013): 790-800.
Stankus, et al. Fabrication of biodegradable elastomeric scaffolds with sub-micron morphologies. J Biomed Mater Res A. 2004;70(4): 603-14.
Stitzel, et al. Controlled fabrication of a biological vascular substitute. Biomaterials. 2006, 27: 1088-1094.

(56) References Cited

OTHER PUBLICATIONS

Stooker, et al. Perivenous application of fibrin glue reduces early injury to the human saphenous vein graft wall in an ex vivo model. European Journal of Cardio-thoracic Surgery. 2002, 21: 212-217.
Traver, et al. New Generation Tissue Sealants and Hemostatic Agents: Innovative Urologic Applications. Reviews in Urology. 2006, 8: 104-111.
Vijayan, et al. Long-term reduction of medial and intimal thickening in porcine saphenous vein grafts with a polyglactin biodegradable external sheath. J Vasc Surg. 2004;40(5): 1011-9.
Wan, et al. Differential, time-dependent effects of perivenous application of fibrin glue on medial thickening in porcine saphenous vein grafts. European Journal of Cardio-thoracic Surgery, 29, (2006): 742-747.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wnek, et al. Electrospinning of nanofiber fibrinogen structures. Nano Letters 3.2 (2003): 213-216.
Xu, et al. Electrospun Nanofiber Fabrication as Synthetic Extracellular Matrix and Its Potential for Vascular Tissue Engineering. Tissue Engineering, vol. 10, No. 7/8, 2004.
Yu, et al. Electrospinning, Encyclopedia of Polymer Science & Technology (2008) 1-20.
Zilla, et al. Constrictive external nitinol meshes inhibit vein graft intimal hyperplasia in nonhuman primates. The Journal of Thoracic and Cardiovascular Surgery 2008;136:717-725.
Zilla, et al. Utilization of shape memory in external vein-graft meshes allows extreme diameter constriction for suppressing intimal hyperplasia: A non-human primate study. J Vasc Surg 2009;49:1532-42.

\* cited by examiner

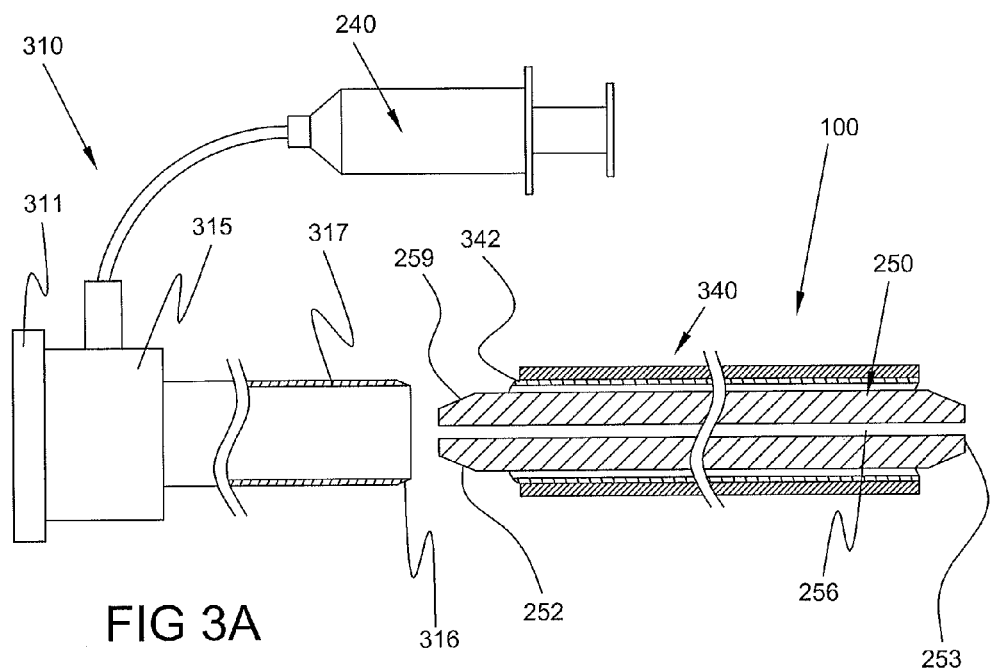
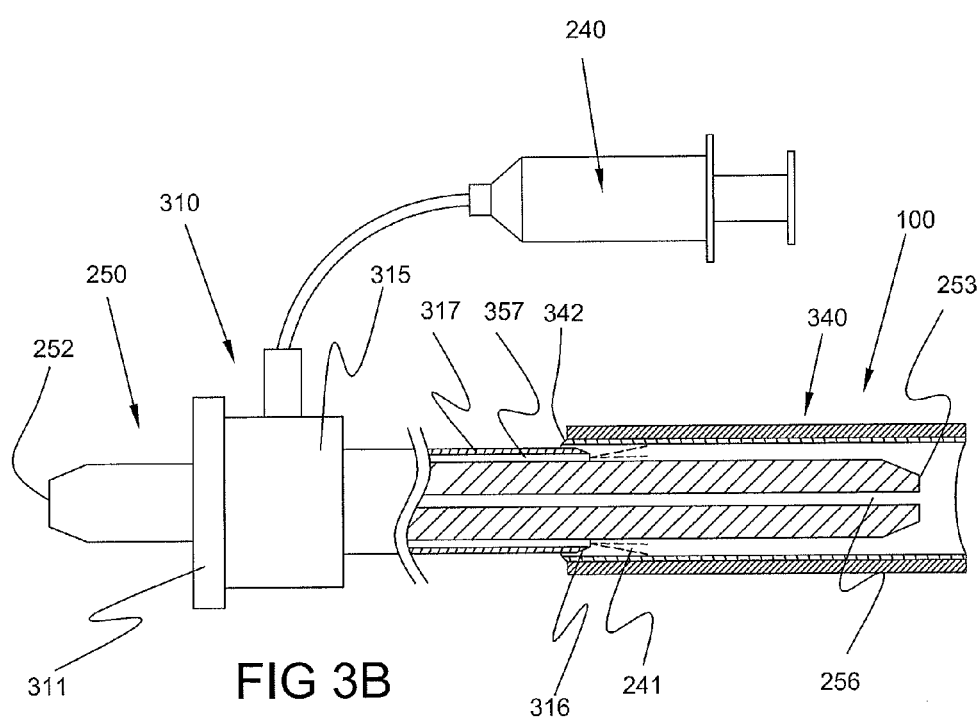

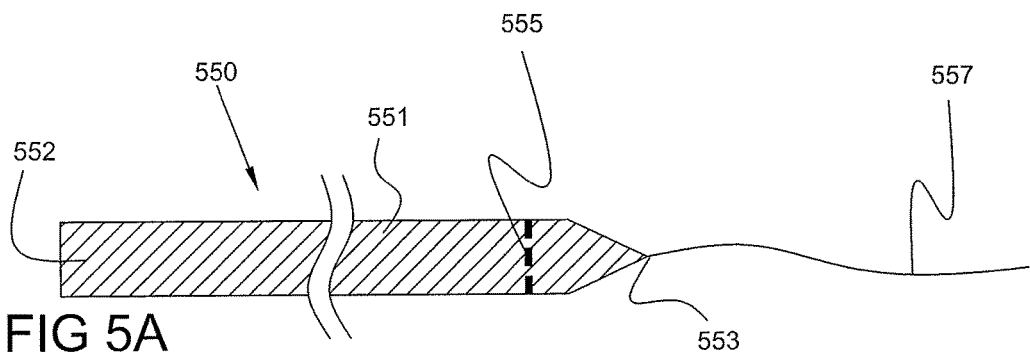
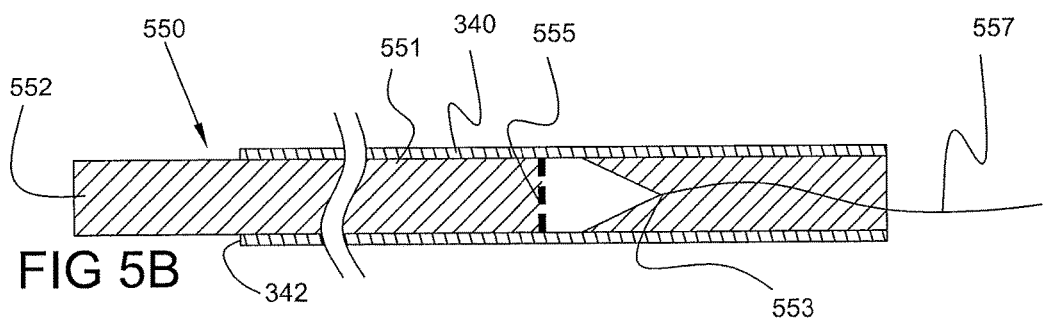
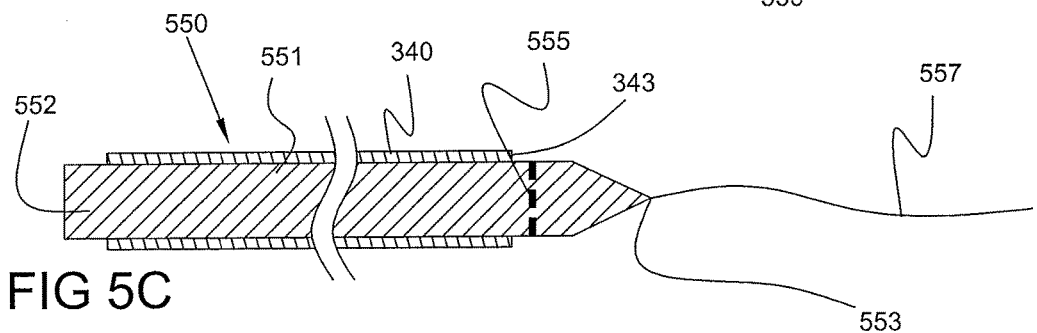
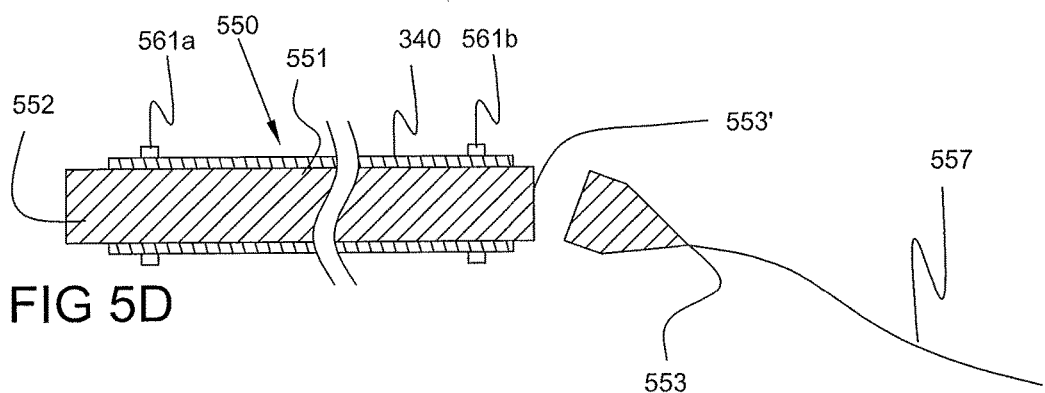

SYSTEM AND MANDREL FOR CREATING GRAFT DEVICES

CROSS-REFERENCE TO RELATED APPLICATIONS

This application is a National Phase application of International Application No. PCT/US12/24251, filed Feb. 8, 2012, which claims benefit of priority to U.S. Provisional Application No. 61/441,078, filed Feb. 9, 2011, the contents of which are hereby incorporated therein by reference in their entirety.

FIELD OF THE INVENTION

The present invention relates generally to systems methods and devices for creating graft devices for a mammalian patient. In particular, the present invention provides a mandrel configured to be atraumatically inserted into a tubular member such as a saphenous vein graft, and an assembly for applying a restrictive fiber matrix to the tubular member.

BACKGROUND OF THE INVENTION

Coronary artery disease, leading to myocardial infarction and ischemia, is currently the number one cause of morbidity and mortality worldwide. Current treatment alternatives consist of percutaneous transluminal angioplasty, stenting, and coronary artery bypass grafting (CABG). CABG can be carried out using either arterial or venous conduits and is the most effective and most widely used treatment to combat coronary arterial stenosis, with nearly 500,000 procedures being performed annually. In addition there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) usually require clinical intervention such as an additional surgery.

IH accounts for 20% to 40% of all AVG failures within the first 5 years after CABG surgery. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

SUMMARY

For these and other reasons, there is a need for systems, methods and devices which provide enhanced AVGs and other grafts for mammalian patients. Desirably the devices will improve long term patency and minimize surgical and device complications. Developing a reliable means to prevent the early events of the IH process can contribute to improvements in the outcome of arterial bypass procedures. Therefore, provided herein is a method of mechanically conditioning and otherwise treating and/or modifying an arterial vein graft, or other tubular member such as living tissue or artificial conduits. To this end, provided herein is a method of applying a restrictive fiber matrix to a tubular member to create a graft device. A mandrel is atraumatically inserted into a tubular member. This assembly is placed in a fiber application device, such as an electrospinning unit, and a restrictive fiber matrix is applied to surround the tubular member. In one particular non-limiting embodiment, the tubular member is tissue, such as saphenous vein tissue, that is to be implanted, for instance, in an arterial bypass procedure, such as a coronary artery bypass procedure.

In one aspect, a system for applying a fiber matrix on a tubular member is provided. The system comprises a fiber matrix delivery assembly; a tubular member; and a mandrel. The fiber matrix delivery assembly is typically an electrospinning device configured to deliver a polymer fiber about the tubular member. The tubular member can comprise living tissue or artificial material, and typically includes a harvested blood vessel. The mandrel comprises a mandrel first end and a mandrel second end. The mandrel is constructed and arranged for atraumatic placement within the tubular member, such as prior to insertion of the mandrel and tubular member assembly into an electrospinning device or other fiber matrix delivery assembly.

The tubular member can comprise a living tissue selected from the group consisting of: vein such as a saphenous vein; artery; lymphatic duct; vas deferens; tear duct; intestine; esophagus; ureter; urethra; trachea; bronchi; duct tissue; Eustachian tube; fallopian tube; and combinations of these. Additionally or alternatively, the tubular member can comprise an artificial conduit selected from the group consisting of: polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these.

The mandrel can comprise a lumen, such as a lumen extending between the mandrel first end and the mandrel second end. The lumen typically comprises a diameter between about 0.005 inches and 0.065 inches, and can be configured to slidingly receive one or more guidewires.

The mandrel can comprise at least a portion that can deliver fluids, such as a portion that includes longitudinally and/or radially distributed side holes or otherwise is porous in construction such that fluids can be delivered prior to insertion of the mandrel, during insertion of the mandrel, and/or during extraction of the mandrel, to or from the tubular member. Fluid can be delivered between the mandrel and the tubular member, and in the case of the tubular member comprising a harvested vein segment, fluid can be delivered in the same direction as the venous flow that was present prior to harvesting of the vein from the patient. In one embodiment, fluid can be delivered to reduce friction during insertion and removal of the mandrel, thus reducing trauma to the tubular member. Alternatively or additionally, fluid can be delivered to perform another function such as a function selected from the group consisting of: hydration of the tubular member; delivery of one or more drugs, cells or other agents to the tubular member; modification of the tubular member; cooling and/or warming of the tubular member; and combinations of these. For example, a lubricous fluid can be delivered through a lumen of the mandrel. A valve can be included, such as a duck-bill or other pressure maintaining valve configured to maintain a fluid pressure within the mandrel or within another system component. Additionally or alternatively, a vacuum source can be included such as a vacuum source configured to maintain a negative pressure between the mandrel and the tubular member.

The mandrel, which can comprise a solid cylinder or hollow tube construction, can be constructed and arranged based on a patient image, such image including but not limited to: an X-ray such as a still image X-ray or fluoroscopy; MRI such as Functional MRI; CT scan; PET Scan; SPECT; Scintigraphy; NMR; Ultrasound; PCT scan; Optical Coherence Tomography (OCT); CCD camera; film camera; and combinations of these.

The mandrel can comprise at least one end with a reduced diameter, such as an end with a tapered profile, an end with a bevel or chamfer, or a radiused end such as an end with a full radius. Each end of the mandrel can comprise a reduced diameter. The mandrel can comprise a solid or hollow tube. The mandrel can comprise a lumen.

The mandrel can comprise at least one end that is removable, such as an end that can be broken off after insertion into a tubular member, or an end that can be disengaged such as via disengagement of one or more of: threads; a frictionally engaging surface; a snap fit; a groove; a recess; and combinations of these. In one embodiment, the removable end comprises an integral guidewire configured to provide an atraumatic insertion of the mandrel into a tubular member.

The mandrel can be configured at one or more ends to engage with a rotational drive of the system, such as a rotational drive of an electrospinning device configured as the fiber matrix delivery assembly. A slot or other recess can frictionally engage a drive shaft, such as a drive shaft of a motor. A snap fit design can be included to engage the rotational drive. In one embodiment, the drive shaft and mandrel engagement portion are mechanically keyed or otherwise include interlocking surfaces. One or more clips can be included to secure an end of the mandrel to a rotational drive, such as clips selected from the group consisting of: a C ring; an E ring; a shaped memory clip; a spring clip; a cotter pin; and combinations thereof. One or more supports can be provided to connect an end of the mandrel to a rotational drive, such as to connect an end of the mandrel to a motor drive shaft.

In one embodiment, the mandrel comprises a braided construction, such as to radially compress when longitudinally elongated and radially expand when longitudinally compressed. Typical insertion includes radial compression of the mandrel prior to insertion into the tubular member, such as to avoid trauma to the tubular member, followed by radial expansion of the mandrel. The magnitude of radial expansion can be chosen to be less than the internal diameter (ID) of the tubular member, approximately the same ID as the tubular member, or greater than the ID of the tubular member. The mandrel can comprise multiple braided filaments such as filaments constructed of materials selected from the group consisting of: stainless steel; Nitinol or other titanium alloys; cobalt-chrome alloys; magnesium alloys; and combinations of these.

In another embodiment, the mandrel comprises a helical construction, such as a helix configured to radially compress when longitudinally elongated and radially expand when longitudinally compressed. Typical insertion includes radial compression of the madnrel prior to insertion into the tubular member, such as to avoid trauma to the tubular member, followed by radial expansion of the mandrel. The magnitude of radial expansion can be chosen to be less than the internal diameter (ID) of the tubular member, approximately the same ID as the tubular member, or greater than the ID of the tubular member. The mandrel can comprise a helix constructed of a Nitinol alloy.

In yet another embodiment, the mandrel comprises a compressible tube, typically a compressible elastomer, constructed and arranged to radially expand when compressed. The mandrel typically includes a threaded rod slidingly received by the compressible tube, and at least one nut that threadingly engages the threaded rod. Rotation of the nut in a first direction around the threaded rod provides a longitudinal compressing force which radially expands the tube. Rotation of the nut in the opposite direction around the threaded rod reduces the longitudinal compressing force which allows radial compression of the tube. Typical insertion includes radial compression of the mandrel prior to insertion into the tubular member, such as to avoid trauma to the tubular member, followed by radial expansion of the mandrel. The magnitude of radial expansion can be chosen to be less than the internal diameter (ID) of the tubular member, approximately the same ID as the tubular member, or greater than the ID of the tubular member.

In yet another embodiment, the mandrel comprises a two-piece construction including an inner tube that is slidingly received by an outer tube. The outer or inner tube can comprise a tapered end configured to reduce trauma during insertion of that tapered end into a tubular member. The inner or outer tube can be of different configurations, such as being made of materials with different properties such as softness; or being constructed in different ways such as tubes having different wall thicknesses. The mandrel is constructed and arranged such that the inner and outer tubes can be positioned such that an end of the inner or outer tube extends beyond the end of the other. The extending end of either the inner or outer tube is first inserted into the tubular member, this extending end being configured for atraumatic insertion. After insertion into the tubular member, the ends of the inner and outer tube can be aligned. In one configuration, at least an end portion of the outer tube is configured to be collapsible, such as to be collapsed for insertion into a tubular member. After insertion, the inner tube, preferably configured more radially rigid than the outer tube's collapsible end portion, is advanced into the end portion, expanding the end portion to a predetermined diameter.

In yet another embodiment, the mandrel is constructed and arranged to radially expand when exposed to a fluid, such as a fluid selected from the group consisting of: saline; a more viscous Newtonian fluid such as glycerin or solutions of dextran in saline; a non-Newtonian fluid such as a hydrogel; a suspension of one or more particulates; and combinations of these. The selected fluid can be a conductive fluid, such as a conductive fluid configured to assist in an electrospinning process in which a charge is applied to the mandrel and/or the conductive fluid. Typical insertion includes insertion of the mandrel into the tubular member prior to swelling of the mandrel by the fluid, such as to avoid trauma to the tubular member. Radial expansion of the mandrel is accomplished with delivery of the fluid. The magnitude of radial expansion can be chosen to be less than the internal diameter (ID) of the tubular member, approximately the same ID as the tubular member, or greater than the ID of the tubular member.

In yet another embodiment, the mandrel comprises a flat sheet configured to be furled. An increase in furling causes a radial compression of the mandrel, while a decrease in furling causes radial expansion of the mandrel. Typical insertion includes radial compression of the mandrel prior to insertion into the tubular member, such as to avoid trauma to the tubular member, followed by radial expansion of the mandrel. The magnitude of radial expansion can be chosen to be less than the internal diameter (ID) of the tubular member, approximately the same ID as the tubular member, or greater than the ID of the tubular member.

In yet another embodiment, the mandrel comprises a telescopic construction. A mandrel first portion with a first diameter is slidingly received by a mandrel second portion with a second diameter. Longitudinal expansion of the mandrel creates an end with a reduced diameter, such as to be atraumatically inserted into a tubular member. Longitudinal compression of the mandrel causes the reduced diameter portion to be contained within the largest diameter portion of the telescopic construction.

The mandrel can include a balloon, such as a balloon surrounding at least a portion of the length of the mandrel. The balloon can be constructed and arranged to be inflated after insertion of the mandrel into the tubular member, and deflated or partially deflated prior to removal from the tubular member. The balloon can include one or more coatings, such as a hydrophilic coating, and the balloon can be conductive and/or be filled with a conductive material.

The mandrel can include a guidewire tip, such as a guidewire J-tip positioned on an end of the mandrel. The guidewire tip can be removable, such as via mechanical engaging means such as threads or by inclusion of a break-away end.

The system can include one or more additional devices or components such as to assist in the delivery of the fiber matrix and/or to reduce the trauma associated with inserting the mandrel into the tubular member.

The system can include a fluid delivery device, such as a device that operably attaches to at least one of the mandrel first end or mandrel second end. The fluid delivery device can include a syringe or a pump, and the fluid delivered can reduce friction between the mandrel and the tubular member such as during insertion and/or retraction of the mandrel into and/or from the tubular member. The fluid can be delivered at a constant flow rate or at a constant pressure. One or more valves can be included, such as a valve configured to allow a shaft, such as the shaft of a mandrel or a guidewire, to pass therethrough while preventing significant loss of fluids around the shaft. The valve can have a touhy-borst construction, and can be configured to maintain fluid pressure in a system component, such as a fluid pressure approximating physiologic arterial pressure. The fluid delivery system can deliver one or more fluids, such as fluids selected from the group consisting of: saline; a lubricous fluid such as silicone gel; a fluid comprising drugs, cells, or other agents; and combinations thereof.

The system can include a tubular member introducer comprising a valve assembly and a hollow tube attached to the valve assembly. The tubular member introducer can slidingly engage the tubular member and deliver one or more fluids, such as to assist in insertion of the mandrel into the tubular member or removal of the mandrel from the tubular member. A fluid delivery device, such as a syringe or a pump, can be included to deliver the one or more fluids. A valve, such as a valve with a touhy-borst construction, can be included to allow passage of one or more shafts such as the shaft of a mandrel or a guidewire, while preventing significant loss of fluids around the shaft. The fluid can be selected from the group consisting of: saline; a lubricous fluid such as silicone gel; a fluid comprising drugs, cells, or other agents; and combinations of these. The tubular member introducer hollow tube can comprise a wall with a thickness less than about 0.100 inches, typically less than about 0.020 inches, and the hollow tube can comprise a tapered or beveled end configured to assist in the insertion of the tubular member introducer into the tubular member. Additionally, the tubular member introducer can maintain an opening in an end of the tubular member, for example the introducer can adhesively grasp an end of the tubular member, thus reducing friction during insertion and removal of the mandrel into and from the tubular member.

The mandrel can comprise a stainless steel material and/or a polymer material. The mandrel can comprise a varied or constant diameter along its length. The mandrel can comprise an approximately linear construction, or the mandrel can comprise at least a portion that is curvilinear.

The mandrel can include a coating along at least a portion of its length, such as a hydrophilic or a hydrophobic coating. The mandrel can include a dissolvable coating, such as a coating including a salt such as sodium chloride, and the coating can be configured to be removed such as to remove the mandrel from the tubular member after the fiber application process is complete. Typical coatings can include one or more agents, such as an agent selected from the group consisting of: friction reducing coatings such as hydrophilic coatings and lubricant coatings; antithrombogenic coatings such as phospholipid coatings, heparin-conjugated group coatings and other drug immobilization coatings; vasoactive coatings such as norepinephrine, papaverine, sodium nitroprusside, nitric oxide, and carbon monoxide agents; and combinations of these. Coatings can be configured to change the mandrel size such as a coating including a superabsorbent hydrogel that swells (e.g. accumulating more water) and/or contracts (e.g. releasing water). The coating can be configured to respond to external triggers such as temperature, electricity, light, pH, and the like. Coatings can be configured to both reduce friction and adjust the diameter of at least a portion of the mandrel.

The system can include a guidewire, such as a guidewire that is slidingly received by one or more lumens of the mandrel or is fixedly attached to an end of the mandrel. The guidewire can include a J-Tip and can include one or more coatings such as a lubricious coating.

The system can include one or more clips constructed and arranged to secure at least one of the mandrel first end or the mandrel second end to at least one of a first end or a second end of the tubular member. The clip is typically a clip selected from the group consisting of: spring clip; tubing clamp; compression ring; tie wrap; and combinations of these.

The system can include a support configured to engage the mandrel first end and/or the mandrel second end. The support can be configured to rotate the mandrel, for example via a rotational drive where the mandrel is operably attached to the rotational drive.

The fiber matrix delivery assembly can comprise a device selected from the group consisting of: an electrospinning unit; a misting assembly; a sprayer; a braiding device; a micropatterning device; an injection device; and combinations of these.

According to another aspect, a method for applying a fiber matrix to a tubular member is provided. A mandrel, comprising a first end and a second end, is atraumatically inserted into the tubular member. A fiber matrix is applied to the tubular member. The tubular member is typically living tissue, such as a harvested blood vessel, or artificial material. The fiber matrix is typically applied with an electrospinning device, a misting assembly, a sprayer, or other fiber matrix delivery device.

In one embodiment, a guidewire, attached to the end of the mandrel or inserted through a lumen of the mandrel, is first inserted into the tubular member such as to help guide the mandrel into the tubular member, for example into a lumen of the tubular member. The tubular member can be positioned relatively vertically, such as to use gravity to assist in the insertion.

The method can include the removal of one or more ends of the mandrel, such as by breaking off an end of the mandrel or disengaging a connection between mandrel portions such as a connection including one or more of: threads; a frictionally engaging surface; a snap fit; a groove; a recess; and combinations of these.

The method can include attaching one or both ends of the mandrel to a rotational drive of the fiber matrix delivery device. The attachment can include the use of a support or clip, such as a support that connects the mandrel to a drive shaft of a motor. A clip can be used to attach the mandrel first end and/or the mandrel second end to the support, for example a clip comprising an attachment element selected from the group consisting of: a C ring; an E ring; a shaped memory clip; a spring clip; a cotter pin; and combinations of these.

The method can include dispensing one or more fluids, e.g. saline, to the internal walls of the tubular member prior to or during insertion of the mandrel into the tubular member. Fluids can be dispensed to reduce friction, hydrate the tubular member and/or deliver one or more drugs, cells or other agents to the tubular member. Fluid can be delivered through the mandrel, such as through a porous portion of the mandrel, or by a device positioned to deliver fluid between the outer wall of the mandrel and the inner wall of the tubular member. Fluid can be dispensed into a balloon surrounding the mandrel. In one embodiment, the tubular member comprises a harvested vein segment, and fluid is delivered in the same direction as venous flow present prior to harvesting.

The method can include attaching a sheath assembly to the mandrel. The sheath assembly can deliver one or more fluids, such as lubricous fluids such as silicone gel, to the mandrel or to a location between the mandrel and the tubular member. Other fluids include: saline; fluids comprising drugs, cells, or other agents; and combinations of these.

The method can include slidingly engaging a tubular member introducer to the tubular member. The tubular member introducer comprises a valve assembly and a hollow tube attached to the valve assembly. One or more fluids can be delivered, such as by a syringe or pump of the tubular member introducer. One or more valves can be included, such as one or more valves with a touhy-borst construction, such that a shaft of the mandrel or a guidewire can be passed through the tubular member introducer while preventing significant loss of fluids around the shaft. The tubular member introducer hollow tube can comprises a wall with a thickness less than about 0.100 inches, typically less than about 0.020 inches, and the hollow tube can comprise a tapered or beveled end configured to assist in the insertion of the tubular member introducer into the tubular member. Additionally, the tubular member introducer can maintain an opening in an end of the tubular member, for example the introducer can adhesively grasp an end of the tubular member, thus reducing friction during insertion and removal of the mandrel into and from the tubular member.

The method can include attaching a fluid delivery device to at least one end of the mandrel, such as a fluid delivery device comprising a syringe or a pump and configured to deliver a fluid to the surface of the mandrel and/or the inner walls of the tubular member. One or more valves can be included, such as one or more valves with a touhy-borst construction, such that a shaft of the mandrel or a guidewire can be passed through the tubular member introducer while preventing significant loss of fluids around the shaft. Continuous pressure can be maintained by the fluid delivery device, such as throughout the mandrel insertion process.

The method can include attaching a sheath assembly to the tubular member where the sheath can comprise a hollow tube with a circumferential wall. The sheath can include a valve, for example a touhy-borst valve, where the mandrel is passed through the valve. The sheath assembly can deliver one or more fluids, such as lubricous fluids, to the mandrel or to a location between the mandrel and the tubular member.

The method can include radially compressing the mandrel, such as a radial compression performed prior to atraumatically inserting the mandrel into the tubular member. Radial compression can include one or more of: deflation of a balloon; longitudinal expansion of a braided mandrel; longitudinal expansion of a helical mandrel; longitudinal expansion of an elongate tube; and dehydration of a mandrel constructed and arranged to swell in the presence of a fluid.

The method can include radially expanding the mandrel, such as a radial expansion performed after the mandrel has been inserted into the tubular member. The magnitude of radial expansion can be chosen to be less than the internal diameter (ID) of the tubular member, approximately the same ID as the tubular member, or greater than the ID of the tubular member. Radial expansion can include one or more of: inflation of a balloon; longitudinal compression of a braided mandrel; longitudinal compression of a helical mandrel; longitudinal compression of an elongate tube; and hydration of a mandrel constructed and arranged to swell in the presence of a fluid.

The method can include attaching a support to at least one end of the mandrel such that the support locks the mandrel diameter.

The method can include inserting an extended end of a mandrel comprising an inner tube and an outer tube, into a tubular member. The method can further include sliding the inner and outer tubes of the mandrel relative to one another, such as to slide an inner tube first end to align with an outer tube first end, such that the inner tube provides a supporting force to the outer tube.

The method can include furling a furlable mandrel such as to radially expand or radially compress the mandrel. Unfurling of the mandrel can be performed to size (e.g. radially expand) the mandrel diameter to the tubular member. The magnitude of radial expansion can be chosen to be less than the internal diameter (ID) of the tubular member, approximately the same ID as the tubular member, or greater than the ID of the tubular member.

The method can include axially lengthening a telescoping mandrel, such as to extend a reduced diameter section, and then to introduce the reduced diameter section atraumatically into a tubular member. Once in place, the mandrel can be axially shortened causing larger diameter sections to enter the tubular member.

The method can include attaching the tubular member to the mandrel, such as via one or more clips selected from the group consisting of: spring clip; tubing clamp; compression ring; tie wrap; and combinations of these.

The method can include harvesting of the tubular member such as a harvesting procedure that harvests tissue selected form the group consisting of: vein such as saphenous vein; artery; lymphatic duct; vas deferens; tear duct; intestine; esophagus; ureter; urethra; trachea; bronchi; duct tissue; Eustachian tube; fallopian tube; and combinations of these. Alternatively or additionally, the tubular member can comprise an artificial conduit comprising a material selected from the group consisting of: polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these.

According to another aspect, a method of removing a mandrel from a tubular member is provided. A mandrel is connected to a removal assembly comprising a sheath, a connector and a fluid delivery device. The mandrel, comprising a first end and a second end, is retracted form the tubular member. Fluid is delivered to the tubular member and/or the mandrel, prior to and/or during removal of the tubular member from the mandrel. In the case of the tubular member comprising a harvested vein segment, fluid can be delivered in the same direction as venous flow present prior to harvesting. Fluid can be delivered through the tubular member via a tubular member introducer, as has been described hereabove.

The method can further include passing one or more shafts through a valve of the removal assembly, such as a touhy-borst valve configured to allow the one or more shafts to pass therethrough while preventing significant loss of fluids around the shaft.

The method can further include retracting the mandrel from the tubular member.

The method can further include cutting a fiber matrix applied to the tubular member, such as with a scalpel, prior to removing the mandrel from the tubular member.

According to another aspect, a mandrel for atraumatic placement within a tubular member is provided where the mandrel comprises a shaft comprising a first end, a second end, a lumen therebetween, and at least a porous portion.

According to another aspect, a mandrel for atraumatic placement within a tubular member is provided where the mandrel comprises a shaft comprising a first end, a second end and a guidewire attached to at least one of the first end or the second end. In some embodiments, the guidewire is configured to be removed.

According to another aspect, a mandrel for atraumatic placement within a tubular member is provided where the mandrel comprises an expandable element configured to be expanded after the mandrel is inserted into the tubular member.

According to another aspect, a mandrel for atraumatic placement within a tubular member is provided where the mandrel comprises a shaft comprising a first end and a second end and a fluid delivery device operably attached to at least one of the first end or the second end.

According to another aspect, a mandrel for atraumatic placement within a tubular member is provided where the mandrel comprises a plurality of braided filaments configured to radially expand when the mandrel is longitudinally compressed.

According to another aspect, a mandrel for atraumatic placement within a tubular member is provided where the mandrel comprises a plurality of helically arranged filaments configured to radially expand when the mandrel is longitudinally compressed.

According to another aspect, a mandrel for atraumatic placement within a tubular member is provided where the mandrel comprises a compressible tube configured to radially expand when compressed.

According to another aspect, a mandrel for atraumatic placement within a tubular member is provided where the mandrel comprises an inner tube and an outer tube configured such that the outer tube is inserted into the tubular member before the inner tube.

According to another aspect, a mandrel for atraumatic placement within a tubular member is provided where the mandrel comprises a shaft configured to radially expand when exposed to a fluid.

According to another aspect, a mandrel for atraumatic placement within a tubular member is provided where the mandrel comprises a flat sheet configured to be furled such that the mandrel radially expands when the flat sheet is unfurled.

According to another aspect, a mandrel for atraumatic placement within a tubular member is provided where the mandrel comprises at least two portions, where a first portion comprises a first diameter and a second portion comprises a second diameter greater than the first diameter, and where the first portion is slidingly received by the second portion.

According to another aspect, a system for applying a fiber matrix on a tubular member is provided including a fiber matrix delivery assembly, a tubular member, a mandrel, an a mandrel insertion device. The mandrel insertion device is constructed and arranged to atraumatically insert the mandrel into the tubular member.

BRIEF DESCRIPTION OF THE DRAWINGS

The foregoing and other objects, features and advantages of the systems and methods, will be more fully understood from the following illustrative description, when read together with the accompanying drawings which are not necessarily to scale. The accompanying drawings, which are incorporated in and constitute a part of this specification, illustrate various embodiments of the present invention, and together with the description, serve to explain the principles of the invention. In the drawings:

FIGS. 3A and 3B illustrate side partial sectional views of an exemplary removal device, and a method of using the removal device to remove a mandrel from a graft device;

FIGS. 5A, 5B, 5C, and 5D illustrate a sequence of side views of an exemplary guidewire tipped solid mandrel, shown in multiple insertion steps;

DETAILED DESCRIPTION

Figure 1:
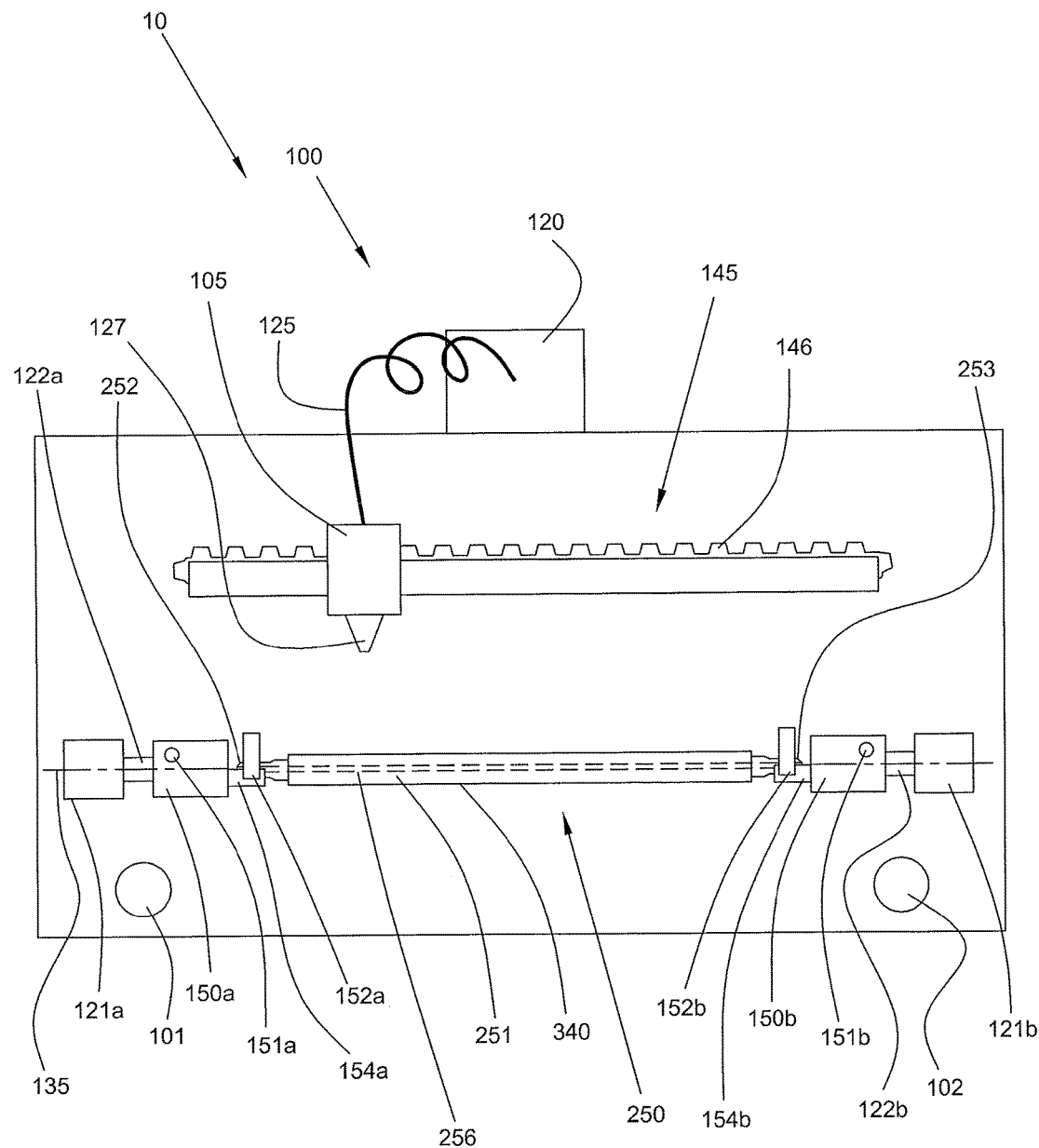
FIG. 1 illustrates a schematic view of an exemplary system for applying a fiber matrix on a tubular member.

Reference will now be made in detail to the present embodiments of the invention, examples of which are illustrated in the accompanying drawings. Wherever possible, the same reference numbers will be used throughout the drawings to refer to the same or like parts.

Provided herein is an apparatus for applying a restrictive fiber matrix to a tubular member. A cartridge device can be included for insertion into a fiber application unit, such as an electrospinning unit or other piece of equipment constructed and arranged to apply a fiber, such as a polymer fiber, around at least a portion of the outer surface of a tubular member, such as a harvested blood vessel. The cartridge device comprises a housing that defines a chamber. Alternatively, the fiber application unit can include a housing that defines a chamber. A tubular member holder, such as a mandrel, is slidingly inserted into the tubular member and this assembly is then inserted into the chamber. The fiber application unit includes a rotational drive mechanism such as a drive including one or more motors, which rotate the assembly of the mandrel and tubular member. While rotating, one or more types of fibers, such as polymer fibers, are delivered by a polymer delivery assembly, typically through at least one nozzle that translates back and forth in an oscillating motion along the length of the tubular member as fiber is applied. One or more nozzles can be included, and each nozzle can deliver a single fiber and/or multiple fibers. The cartridge or other surrounding chamber is sterile and maintains sterility of the tubular member and applied fiber throughout the process.

The graft device produced by the systems, methods and devices of the present invention includes a tubular member and a surrounding fiber matrix covering. The tubular member is typically a hollow tube conduit used as a means for fluid to flow between a first body space and a second body space in a patient. The tubular member can comprise tissue, such as autologous, allogeneic, or xenogeneic tissue, including, without limitation: vein; artery; lymphatic duct; vas deferens; tear duct; intestine; esophagus; ureter; urethra; trachea; bronchi; duct tissue; Eustachian tube; fallopian tube; and combinations of these (meaning the entire structure or a portion of those tissues). The tubular member can also be a tissue engineered vascular graft, comprised of a covering material (biological or synthetic-based) that is seeded with adult differentiated cells and/or undifferentiated stem cells, or unseeded. The covering can be treated with synthetic, biological, or biomimetic cues to enhance antithrombogenicity or selective or non-selective cell repopulation once implanted in vivo. The covering can be treated with one or more chemotactic or chemoattractant agents and can include selective degradation sites. Alternatively or additionally, the tubular member can include an artificial, non-tissue, structure, such as polytetrafluoroethylene (PTFE); expanded PTFE (ePTFE); polyester; polyvinylidene fluoride/hexafluoropropylene (PVDF-HFP); silicone; polyethylene; polypropylene; polyester based polymer; polyether based polymer; thermoplastic rubber; and combinations of these. The graft device can have a relatively uniform cross section, or a cross section that varies (e.g. in diameter or cross sectional geometry) along the length of the tubular member. The graft device can be straight or curved. Additional graft devices, systems and methods are also described in applicant's Provisional Application Ser. No. 61/365,612, filed Jul. 19, 2010, entitled "Graft Devices and Methods of Use", applicant's co-pending PCT Patent Application Serial No. PCT/US2010/60667, filed Dec. 16, 2010, entitled "Graft Devices and Methods for Use", applicant's co-pending PCT Patent Application Serial No. PCT/US2010/62487, filed Dec. 30, 2010, entitled "Graft Devices and Methods of Fabrication", and applicant's co-pending U.S. Provisional Patent Application Ser. No. 61/432,914, filed Jan. 14, 2011, entitled "Apparatus for Creating Graft Devices", each of which are incorporated by reference herein in its entirety.

The applied fiber is typically a polymer or polymer blend fiber that is applied when the one or more polymers are mixed with one or more solvents. Alternatively or additionally, polymers can be applied in liquid form achieved through other means such as by elevated temperature or by the use of monomers which are activated and polymerized during or shortly after processing. Typical polymers include natural polymers, synthetic polymers, and blends of natural and synthetic polymers. For example and without limitation, natural polymers include: silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers.

As used herein, the descriptor "tubular member" does not refer specifically to a geometrically perfect tube having a constant diameter and a circular cross-section. It also embraces tissue and artificial conduits having non-circular and varying cross sections, and can have a variable diameter, and thus any shape having a contiguous wall surrounding a lumen (that is, they are hollow), and two openings into the lumen such that a liquid, solid or gas can travel from one opening to the other. The openings can be at the end of the conduit, or at any location along the length of the conduit. The tubular member can be created from a membranous material, such as a membrane that comprises a sheet that is joined along a seam to create a substantially cylindrical form. The tubular member can comprise harvested tissue that is formed or reformed into a tube or other structure.

The covering typically is substantially or essentially contiguous about an internal or external wall of a tubular member, meaning that the covering forms a continuous, supportive ring on a surface and about a circumference of a portion, but not necessarily over the entire surface (e.g., length) of the tubular member. The covering can be "restrictive", meaning that the covering is in substantial contact with the outer surface of the tubular member such as to provide an incremental physical property in addition to the underlying property of the tubular member. Alternatively, the covering can be narrowly spaced and proximate to the outer surface of the tubular member (e.g. to restrict after an initial unrestricted expansion). The covering can also be "constrictive", meaning that the diameter of the tubular member is reduced by the application of the covering. Restrictive coverings can be used to reinforce, restrict, hinder and/or prevent substantial circumferential and/or longitudinal expansions of the tubular member, such as when the graft device is a tubular member used as a bypass graft and is exposed to arterial pressure; or otherwise when the tubular member is radially and/or longitudinally expanded. The degree of restriction by the covering typically is such that when exposed to internal pressure, such as typical arterial pressures, the tubular member is prevented from distending to the extent that would occur without such restriction. Constrictive coverings can be used to match the internal diameter of the tubular member to the internal diameter of the target tissue being connected by the tubular member. For example, quite often a vein being used as a coronary artery bypass graft has a considerably larger internal diameter than the target coronary artery being bypassed. In order to reduce flow disturbances, it is advantageous to match the internal diameter of the graft (conduit) to the internal diameter of the bypassed coronary artery. The covering can be durable or temporary, such as when the restrictive nature of a biodegradable covering can decline over time. The covering can have a relatively uniform cross section, or a cross section that varies along the length of the covering.

The covering can be applied to a tubular member that has either a cylindrical or non-cylindrical (e.g. oval) mandrel inserted in its lumen. Mandrels are typically constructed and arranged to be removed from the graft device of the present invention without damaging the tubular member or any other portion of the graft device. The mandrel can comprise an expandable tube, such as a furled tube or other radially or longitudinally expandable structure, such that the mandrel can be unfurled or otherwise radially or longitudinally constricted for atraumatic removal from the tubular member of the graft device. The mandrel can transform from a rigid state to a flexible state, and vice versa. Mandrels can have relatively constant cross-sectional geometries, or cross-sections that vary, such as mandrels including a first portion with a circular cross section and a second portion with an oval cross section. Mandrels can include one or more tapered ends, and it can include a tapered segment.

The mandrel can be relatively straight, or can have a non-linear geometry. In one embodiment, a mandrel comprises a three dimensional geometry intended to match anatomical locations of a patient, such as an anatomical topography proximate two or more intended anastomotic connections for the graft device. Mandrels can include both straight and curved portions. The mandrel can be a malleable or otherwise deformable structure which is shaped, such as a shaping prior to, during or after application of the fiber matrix to a tubular member. The mandrel can be shaped or otherwise fabricated based upon one or more patient images created during an imaging procedure, such as an imaging procedure selected from the group consisting of: X-ray such as still image X-ray or fluoroscopy; MRI (including Functional MRI), CT scan, PET Scan, SPECT, Scintigraphy, NMR, Ultrasound, PCT scan, Optical Coherence Tomography (OCT), CCD camera; film camera; and combinations of these.

In coverings applied to a tubular member with an electrospinning process, an electrically conductive mandrel, for example, a rod that is formed of a conductive material such as stainless steel, can be placed inside a tubular member, such as a vein, and polymer fibers deposited about the circumference of at least a portion of the tubular member by rotation or other movement of the mandrel, movement of the nozzles supplying the fiber, and/or movement of the electrical field directing the fibers toward the mandrel. Thickness, as well as other mechanical and physical properties of the covering, can be controlled by adjusting the chemical or physical properties of the polymer solution to be deposited (e.g. adjusting the conductivity, surface tension and/or viscosity of the solution), varying the infusion rate of the polymer solution, modifying the electric field between the polymer source and the mandrel or target, and/or adjusting duration of the electrospinning. Use of a more or less viscous polymer compositions can result in thicker or thinner fibers, respectively, affecting the mechanical properties (e.g. the elastic, viscoelastic, and plastic properties), the level of polymer crystallinity, the solvent content (the amount and feature of nodal points obtained by solvent bonding also affects the mechanical and physical properties of the material), and the porosity of the deposited polymer. The thickness of the covering and fibers within the covering can be selected to determine numerous device properties including but not limited to: stiffness and buckling stability; mechanical stability under sustained levels of stress of cyclic deformations; speed of biodegradation of the covering; permeability of the material; and combinations of these. Biodegradation can also be varied by altering the surface finish, wettability, porosity or other characteristic of the fibers, as well as by introducing functional domains to the fiber matrix structure (e.g., cleavage domains activated in response to natural or artificial cues). These parameters can be altered by using solvents or diluents that evaporate at varying rates and/or by adding purifiers to the solution, such as immiscible fluids, emulsified particles or undissolved solids that can be later dissolved such as to create pores. Alternatively or additionally, other modifying agents can be added to the polymer prior to electrospinning such as detergents or surfactants. These polymer solution parameters are optimized, depending on the end-use of the covering, to achieve a desired or optimal physiological effect. Functional domains can be added by covalent bonding to the fiber matrix structure. Thickness and other features (e.g. fiber size, porosity, nodal points, fiber crystallinity or mechanical properties) can be varied along the length of a target in a regular or irregular fashion, such as in creating a target that is thicker at one or both ends, in the center or as with a location-dependent symmetrical or asymmetrical thickness. In another particular embodiment, the thickness is varied by moving an electrospinning nozzle back and forth slowly near a specific circumferential location, thereby depositing more material proximate to that area or to create recurring features. In yet another particular embodiment, covering thickness is determined by the thickness of the tubular member, such as when the covering is thicker at a circumferential portion of the tubular member that is thinner than other circumferential portions of the tubular member. In still yet another particular embodiment, thickness and/or other properties are varied by applying a field modification proximate to the polymer source or target to alter the trajectory of the fibers. Such a field modification can be produced, for example, by a metal plate that is inserted into the area adjacent to the source or target that is at a sufficiently different voltage potential than the source such that the resulting field alters the trajectory of the fibers.

Electrospinning can be performed using two or more nozzles, wherein each nozzle can be a source of a different polymer solution. The nozzles can be biased with different biases or the same bias in order to tailor the physical and chemical properties of the resulting non-woven polymeric mesh. Additionally, multiple different targets (e.g. multiple mandrels) can be used. When the electrospinning is to be performed using a polymer suspension, the concentration of the polymeric component in the suspension can also be varied to modify the physical properties of the matrix. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower polymer concentration solutions have a lower viscosity, leading to greater extrusion or attenuation of the fibers to produce thinner fibers. One skilled in the art can adjust polymer solution chemical and physical properties and process parameters to obtain fibers of desired characteristics, including fibers whose characteristics change along the length or width of the target.

Coverings can be constructed and arranged in a manner specific to a patient morphological or functional parameter. These parameters can be selected from the group consisting of: vessel size such as inside diameter, outside diameter, length, and/or wall thickness of the vessel; taper or other geometric property of a harvested vessel or vessel intended for anastomotic attachment; size and location of one or more side branch ostium or antrum within the harvested vessel; patient age or sex; vessel elasticity or compliance; vessel vasculitis; existing varicosities and other vascular pathologies; vessel electrical impedance; specific patient genetic factors or traits; specific patient pathologies; and combinations of these.

Coverings of arterial vein grafts can be processed in a way to achieve a certain blood flow rate or shear stress within the treated arterial vein graft. In a typical configuration, shear stress within the arterial vein graft is between 2 dynes/cm$^2$ to 30 dynes/cm$^2$, preferably 12 dynes/cm$^2$ to 20 dynes/cm$^2$ is achieved. Coverings can be processed in a way to control the oxygen, nutrients, or cellular permeabilities between the extravascular tissues and the abluminal surface of the treated hollow tissue. Such permeabilities depend on the covering chemical and physical properties, the pore size distribution, porosity, and pore interconnectivity. Generally, oxygen, nutrients, and cellular (e.g., angiogenesis related cells, pericytes, endothelial cells, endothelial progenitor cells, inflammation-related cells; macrophages, etc.) permeability are required to improve the treated hollow tissue in vivo remodeling and healing process. To this end, the pore size range is typically between 1 microns and 1000 microns, preferably between 100 microns and 250 microns, and the porosity range typically between 50% and 95%, preferably between 60% and 90%. Pore size and other porosity parameters can be achieved through one or more post-processing steps performed after electrospinning or other fiber application process. Porosity can be adjusted with a mechanical tool such as a microneedle punch assembly, with energy such as with a laser and/or chemically such as with an etching or other material removal process. The pores preferably are highly interconnected so that a relatively straight path along the radial direction of the fiber matrix can be traced from most of the pores across the total thickness of the matrix. Polymers used are typically hydrophobic.

Radial restriction and constriction of saphenous vein grafts has been achieved with stent devices placed over the vein prior to anastomosing the graft to the targeted vessels. The devices of the present invention provide numerous advantages over the stent approaches. The devices of the present invention can have one or more parameters easily customized to a parameter of the harvested vessel and/or another patient parameter. The covering can be customized to a harvested vessel parameter such as geometry, such as to reduce the vein internal diameter to produce desired flow characteristics. The covering can be customized to other harvested vessel parameters such as the number and location of side branches or other vessel irregularities, such as to produce an internal lumen with a consistent size along the length of the graft despite the external irregularities of the harvested vessel. The covering can be customized to a target vessel parameter (e.g., the aorta and diseased artery), such as to be compatible with vessel sizes, mechanical properties, and/or locations. The covering can be modified to simplify or otherwise improve the anastomotic connections, such as to be reinforced in the portion of the device that is anastomosed (e.g., portion where suture and/or clips pass through) and/or to protrude beyond the length of the tubular member and overlap other members connected to the graft device.

The devices of the present invention can be made to a wide array of lengths during the procedure, without the need for cutting, such as the cutting of a stent device, which might create dangerously sharp edges. The covering is applied to the tubular member in a controlled, repeatable manner, by an apparatus such as an electrospinning instrument. The ends of the covering are atraumatic, avoiding tissue damage or irritation at the anastomotic sites. In addition, the coverings of the present invention can be constructed and arranged to be easily and atraumatically removable, such as to apply another covering. Stent devices are applied manually by a clinician, require significant manipulation which could cause iatrogenic damage, have issues with reproducibility and accuracy limitations, and are difficult to reposition or remove, particularly without damaging the harvested vessel. The conformal covering follows the natural external geometry of the vessel (e.g., adventitial tissue accumulations, ligated branches, etc.) without resulting in a net inward compression caused by external application of a constant tubular structure onto a naturally variable tubular tissue.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, the term "polymer composition" is a composition comprising one or more polymers. As a class, "polymers" includes homopolymers, heteropolymers, co-polymers, block polymers, block co-polymers, alloys or blends and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

The polymer or polymers typically can be selected so that it degrades (e.g. it is bioabsorbed, has decreased mechanical strength and/or otherwise changes one or more mechanical properties) in situ over a time period to optimize mechanical conditioning of the tissue or other tubular member. Non-limiting examples of useful in situ degradation rates include between 2 weeks and 1 year, and increments of 1, 2, 4, 8, 12, and, 24 weeks therebetween. Biodegradation can occur at different rates along different circumferential and/or longitudinal portions of the covering. A biodegradation rate of the polymer covering can be manipulated, optimized or otherwise adjusted so that the covering degrades over a useful time period. For instance, in the case of a coronary artery bypass, it is desirable that the covering dissolves over 2 weeks or, more typically, 10 weeks or more, so as to prevent substantial sudden circumferential wall stress on the graft. The polymer degrades over a desired period of time so that the mechanical support offered by the polymer covering is gradually reduced over that period and the vein would be exposed to gradually increasing levels of circumferential wall stress (CWS).

The biodegradable and non-biodegradable polymers useful herein also can be elastomeric. Generally, any elastomeric polymer that has properties similar to that of the soft tissue to be replaced or repaired is appropriate. For example, in certain embodiments, the polymers used to make the wrap are highly distensible. Non-limiting examples of suitable polymers include those that have plastic yield strain of 10% to 100% and breaking strain of from 100% to 1700%, more preferably plastic yield strain between 15% and 100%, and breaking strain between 200% and 800%, and even more preferably plastic yield strain between 50% and 100%, and breaking strain between 200% and 400%. Further, it is often useful to select polymers with ultimate tensile stress between 10 kPa and 30 MPa, more preferably between 5 MPa and 25 MPa, and even more preferably between 8 MPa and 20 MPa. In a typical embodiment, polymeric fiber matrices with plastic yield tensions between 1 N/cm and 10 N/cm, preferably between 2 N/cm and 5 N/cm are used. In certain embodiments, the elastic modulus calculated for physiologic levels of strain is between 10 kPa to 100 MPa, more preferably between 0.5 MPa and 1.5 MPa, and even more preferably between 0.5 MPa and 1.0 MPa.

As used herein, a "fiber" comprises an elongated, slender, thread-like and/or filamentous structure with or without branching fibers. Fibers can be solid (including composite materials such as concentric or particulate-included composite materials) or hollow, and can have a smooth, rough, or porous surface.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

Referring now to FIG. 1, a schematic view of a system for applying a fiber matrix on a tubular member, to create a graft device, is illustrated. System 10 includes electrospinning unit 100 and mandrel 250. Mandrel 250 has been atraumatically inserted into conduit 340. Conduit 340 can comprise living tissue and/or artificial materials, as has been described in detail hereabove. Electrospinning unit 100 includes nozzle assembly 105 including nozzle 127 which is configured to deliver one or more fibers to conduit 340 to create the fiber matrix covering.

Mandrel 250 comprises a shaft 251 with first end 252 and second end 253. Lumen 256 extends from end 252 to end 253. In an alternative embodiment, one or both ends of lumen 256 can exit through a side hole in mandrel 250. Mandrel 250 can include a coating, along at least a portion of its length, such as a hydrophilic or a hydrophobic coating. Mandrel 250 can include a dissolvable coating, such as a coating including a salt such as sodium chloride, and configured to be removed such as to remove mandrel 250 from conduit 340 after the fiber application process is complete. Mandrel 250 can include a coating comprising one or more agents, such as an agent selected from the group consisting of: friction reducing coatings such as hydrophilic coatings and lubricant coatings; antithrombogenic coatings such as phospholipid coatings, heparin-conjugated group coatings and other drug immobilization coatings; vasoactive coatings such as norepinephrine, papaverine, sodium nitroprusside, nitric oxide, and carbon monoxide agents; and combinations of these. Coatings can be configured to change the mandrel size such as a coating including a super-absorbent hydrogel that swells (e.g. accumulating more water) and/or contracts (e.g. releasing water). The coating can be configured to respond to external triggers such as temperature, electricity, light, pH, and the like. Coatings can be configured to both reduce friction and adjust the diameter of the mandrel. Lumen 256 is typically sized for a guidewire, such as a standard interventional guidewire with a diameter ranging between about 0.005 inches to 0.065 inches. Lumen 256 can include one or more coatings, such as a lubricous coating, a hydrophilic coating and/or a hydrophobic coating. Mandrel end 252 comprises a tapered cross sectional profile, such as to be atraumatically inserted into conduit 340 prior to insertion of mandrel 250 into electrospinning unit 100. Mandrel end 253 can also comprise a tapered cross section, as is shown in FIG. 1, or a different atraumatic end geometry such that either end of mandrel 250 can be atraumatically placed into conduit 340. Mandrel end 252 is typically free from sharp edges, burrs, and other potentially traumatic geometries or conditions.

Ends 252 and 253 are positioned to rest in projections 154a and 154b of supports 150a and 150b, respectively. Supports 150a and 150b are fixedly attached to shafts 122a and 122b of motors 121a and 121b. Motors 121a and 121b comprise a drive assembly of electrospinning unit 100, such as a synchronous drive assembly, configured to rotate mandrel 250 during the electrospinning process. Pins 151a and 151b pass through supports 150a and 150b, respectively, and engage supports 150a and 150b to motor shafts 122a and 122b, respectively. Ends 252 and 253 are frictionally engaged with projections 154a and 154b by clips 152a and 152b, respectively.

Figure 1A:
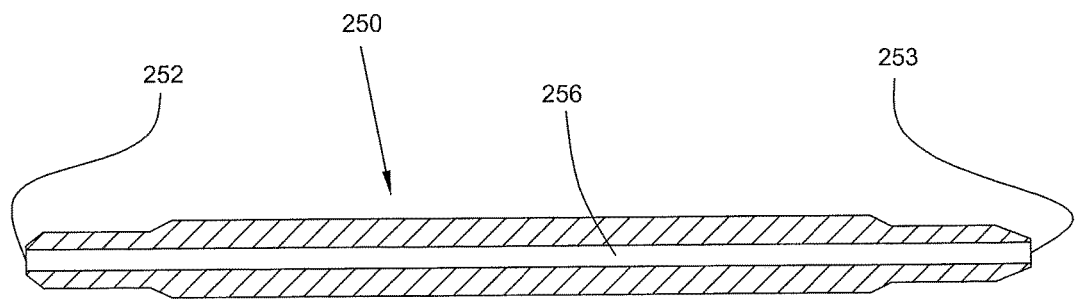
FIG. 1A illustrates a side sectional view of the mandrel of FIG. 1.

Referring additionally to FIG. 1A, a side sectional view of mandrel 250 is illustrated, including ends 252 and 253, as well as lumen 256. Lumen 256 is configured to allow a shaft, such as a guidewire shaft, to pass therethrough, such as to allow the guide wire to be first inserted into a conduit (e.g., conduit 340 of FIG. 1), to be followed by end 252 or end 253. This insertion technique reduces trauma to the conduit during the mandrel 250 insertion process.

Figure 1B:
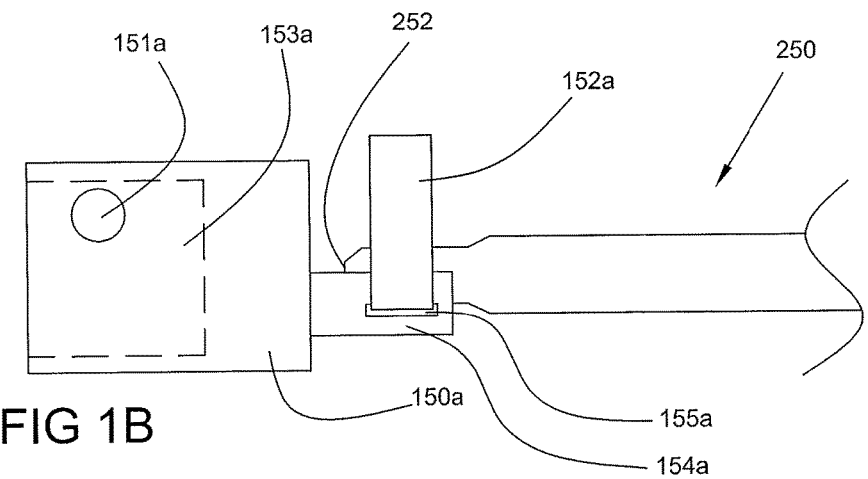
FIG. 1B illustrates a side view of a portion of the mandrel of FIG. 1 with attached support member.

Referring additionally to FIG. 1B, a side view of a portion of mandrel 250 with attached support member is illustrated. Support 150a includes slot 153a, configured to slidingly receive a shaft (e.g., shaft 122a of FIG. 1) of a motor (e.g., motor 121a of FIG. 1). Engaging pin 151a passes through support 150a and engages a surface, such as a recess (not shown), to mechanically lock support 150a to the shaft. Mandrel 250 includes end 252 which is nested in projection 154a of support 150a. Clip 152a surrounds end 252 and engages groove 155a such as to frictionally engage mandrel 250 to support 150a and thus the motor shaft.

Figure 1C:
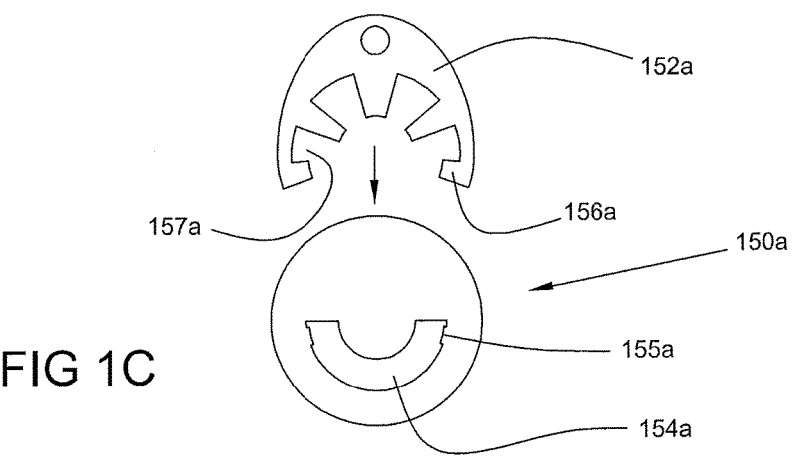
FIG. 1C illustrates an end view of a mandrel clip and support member.

Referring additionally to FIG. 1C, an end view of support 150a is shown with clip 152a above and ready to be engaged with support 150a. Mandrel 250 has been omitted for illustrative clarity. Clip 152a includes one or more recesses 157a configured to improve flexing of clip 152a during attachment and/or removal from support 150a. Clip 152a further includes nub 156a which is configured to engage with a groove, recess 155a of projection 154a. Clip 152a can include various configurations including attachment components selected from the group consisting of: a C ring; an E ring; a shaped memory clip; a spring clip; a cotter pin; and combinations of these.

Referring to FIG. 1, mandrel 250 is positioned in a particular spaced relationship from nozzle assembly 105 and nozzle 127. For example, mandrel 250 can be positioned above (as shown) or below nozzle assembly 105. In some embodiments, mandrel 250 is located to the right or left of nozzle assembly 105. The distance between mandrel 250 and the tip of nozzle 127 is typically less than 20 cm, more typically less than 15 cm. In a particular embodiment, the tip of nozzle 127 is approximately 12.5 cm from mandrel 250. Alternatively, multiple nozzles (not shown), for example nozzles of similar or dissimilar configurations, can be positioned in various orientations relative to mandrel 250. Two or more of the multiple nozzles can each deliver one or more fibers to conduit 340 and/or mandrel 250, such as multiple fibers delivered simultaneously or sequentially.

Nozzle 127 can be constructed of stainless steel. In one embodiment, nozzle 127 has a tubular construction with a length of approximately 1.5", an ID of approximately 0.047 inches and an OD of approximately 0.065 inches. In one embodiment, nozzle 127 has an ID between about 0.047 inches and 0.055 inches. Nozzle 127 can be generally cylindrical and configured about a straight axis. Alternatively, nozzle 127 can be oval or configured with multiple openings aligned along a straight line or otherwise. Nozzle 127 can include an insulating coating, with the tip of nozzle 127 exposed (e.g. non-insulated), such as with an exposed length of approximately 1 cm. Nozzle geometry and electrical potential voltages applied between nozzle 127 and mandrel 250 are chosen to control fiber generation. In a typical embodiment, fibers are created with a diameter between 0.1 µm and 2.0 µm, more typically with a diameter between 0.1 µm and 1.0 µm.

An electrical potential can be applied between the nozzle 127 and one or both of conduit 340 and mandrel 250. The electrical potential can draw at least one fiber from the nozzle assembly 105 to the conduit 340. The conduit 340 can act as the substrate for the electrospinning process, collecting the fibers that are drawn from nozzle assembly 105 by the electrical potential.

In some embodiments, mandrel 250 and/or conduit 340 has a lower voltage than nozzle 127, to create the electrical potential. For example, the voltage of mandrel 250 and/or conduit 340 can be a negative or zero voltage while the voltage of the nozzle 127 can be a positive voltage. Mandrel 250 and/or conduit 340 can have a voltage of about −5 kV (e.g., −10 kV, −9 kV, −8 kV, −7 kV, −6 kV, −5 kV, −4.5 kV-4 kV, −3.5 kV, −3.0 kV, −2.5 kV, −2 kV, −1.5 kV, −1 kV) and nozzle assembly 105 can have a voltage of about +15 kV (e.g., 2.5 kV, 5 kV, 7.5 kV, 12 kV, 13.5 kV, 15 kV, 20 kV). In some embodiments, the potential difference between nozzle assembly 105 and mandrel 250 and/or conduit 340 can be from about 5 kV to about 30 kV. This potential difference draws fibers from nozzle assembly 105 to the conduit 340. In a preferred embodiment, nozzle 127 is placed at a potential of +15 kV while mandrel 250 is placed at a potential of −5 kV. The potential difference between nozzle assembly 105 and mandrel 250 and/or conduit 340 can be varied during the application of the fiber matrix.

A polymer solution, stored in a sterile condition in polymer solution dispenser 120, can be delivered to nozzle assembly 105 through a polymer solution delivery tube 125. The electrical potential between nozzle 127 and conduit 340 and/or mandrel 250 can draw the polymer solution through nozzle 127 of nozzle assembly 105. Electrostatic repulsion, caused by the fluid becoming charged from the electrical potential, counteracts the surface tension of a stream of the polymer solution at nozzle 127 of nozzle assembly 105. After the stream of polymer solution is stretched to its critical point, one or more streams of polymer solution emerges from nozzle 127 of nozzle assembly 105, and/or at a location below nozzle assembly 105, and move toward the negatively charged conduit 340. Using a volatile solvent, the solution dries substantially during transit, and the fiber is deposited on conduit 340.

Mandrel 250 is configured to rotate about an axis 135, with nozzle 127 perpendicular to axis 135. The rotation around axis 135 allows the fiber matrix to be deposited along all sides, or around the entire circumference of the conduit 340. Mandrel 250 can be rotated by at least one motor 121*a* and/or 121*b* in direct or indirect communication with the ends of mandrel 250. In some embodiments, the electrospinning unit includes a single motor that rotates one end of mandrel 250. In some embodiments, two motors 121*a*, 121*b* are used. For example, motor 121*a* can be in communication with one end of mandrel 250 while motor 121*b* is in communication with the opposite end of mandrel 250. The rate of rotation of mandrel 250 can depend on how the fiber matrix needs to be applied to conduit 340. For example, for a thicker fiber matrix, the rotation rate can be slower than if a thinner fiber matrix is desired. Rotational velocity of mandrel 250 can be varied during the application of the fiber matrix.

In addition to mandrel 250 rotating around axis 135, nozzle assembly 105 can move, such as when driven by drive assembly 145 in a reciprocating or oscillating horizontal motion. Drive assembly 145 comprises a linear drive assembly, such as a belt driven drive assembly comprising belt 146, driven by two or more motor actuated pulleys (motors and pulleys not shown, but configured to cause belt 146 to move in one or two directions). Nozzle assembly 105 is operably engaged to belt 146 such that movement of belt 146 causes equal movement of nozzle assembly 105. Additionally or alternatively, nozzle assembly 105 can be constructed and arranged to rotate around axis 135, rotating means not shown. Additionally or alternatively, mandrel 250 can be constructed and arranged to oscillate in a horizontal (i.e. axial) direction. The length of the drive assembly and the linear motion applied to nozzle assembly 105 can vary based on the length of the tubular member to which a fiber matrix can be delivered. For example, the supported linear motion of the drive assembly can be about 10 cm to about 50 cm. Nozzle assembly 105 can move along drive assembly 145 to apply a fiber matrix to the entire length, or specific portions of a length, of conduit 340. In one embodiment, fiber is applied to the entire length of conduit 340 plus an additional 5 cm (to mandrel 250) on either end of conduit 340. In another embodiment, fiber is applied to the entire length of conduit 340 plus at least 1cm beyond either end of conduit 340.

Nozzle assembly 105 can be controlled such that specific portions along the length of conduit 340 are reinforced with a greater amount of fiber matrix as compared to other or remaining portions. In addition, conduit 340 can be rotating around axis 135 while nozzle assembly 105 is moving along drive assembly 145 to provide control over the location on conduit 340 where the fiber matrix will be applied. In a typical embodiment, nozzle assembly 105 is translated back and forth by belt 146 at a velocity of approximately 200 mm/sec. Rotational speeds of mandrel 250 and translational speeds of nozzle assembly 105 can be relatively constant, or can be varied during the application of the fiber matrix.

System 10 can also include a power supply, not shown, but configured to provide the electric potentials to nozzle 127 and mandrel 250, as well as supply power to other components of system 10. The power supply can be connected, either directly or indirectly, to at least one of mandrel 250 and conduit 340. Power can be transferred from the power supply to mandrel 250 and/or conduit 340 by, for example, a wire.

System 10 can also include inlet port 101 and/or outlet port 102. Ports 101 and 102 can be used to control the environment surrounding nozzle 127 and/or mandrel 250. Ports 101 and/or 102 can be configured to be both an inlet port and an outlet port. System 10 can include a housing, not shown but typically attachable to electrospinning unit 100 and defining a chamber surrounding nozzle 127 and/or mandrel 250, such that ports 101 and 102 can control a more limited (smaller) environment surrounding nozzle 127 and/or mandrel 250. Ports 101 and 102 can be used to introduce or remove one or more gases, introduce or remove humidity, control temperature, control pressure; maintain or control sterility; and provide other environmental controls.

The distal end of nozzle 127 can be positioned vertically offset from the axis 135 of mandrel 250. Typically offsets are chosen between about 1.0 cm and 5.0 cm and prevent any polymer solution or other material that falls from nozzle 127, due to gravity or another force, from undesirably landing on mandrel 250 and/or conduit 340.

In addition or as an alternative to electrospinning unit 100, other devices can be used to apply a fiber matrix to or otherwise reinforce a tubular member that has been placed around a mandrel such as devices selected from the group consisting of: a fiber spraying device; a misting device; a braiding device; a micropatterning device; an injection device; and combinations of these.

Figure 2A:
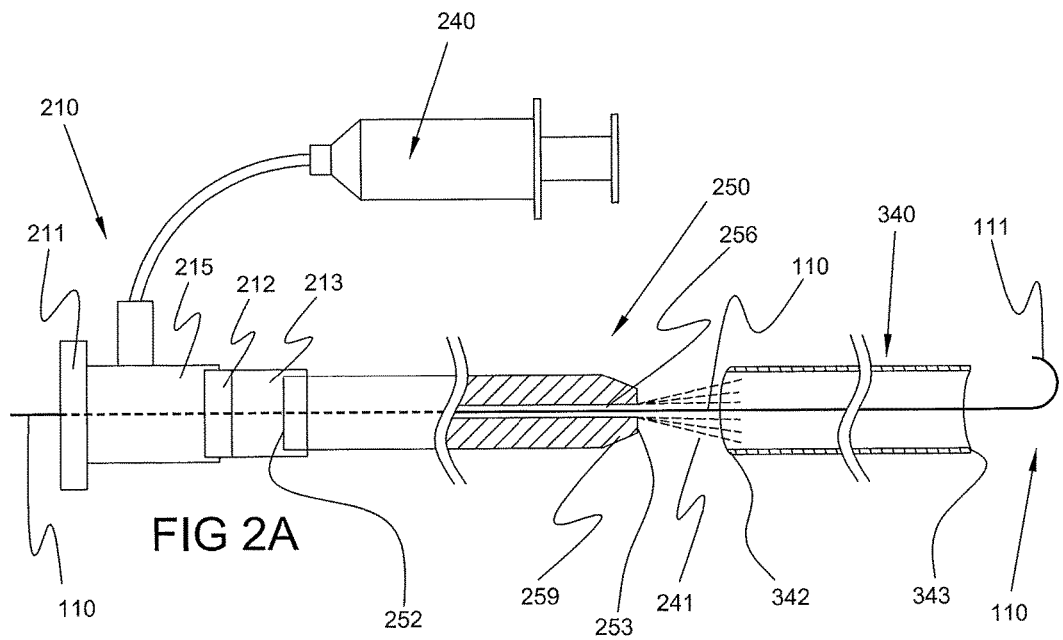
FIGS. 2A and 2B illustrate side partial sectional views of an exemplary insertion device, and a method of using the insertion device to insert a mandrel into a tubular member.
Figure 2B:
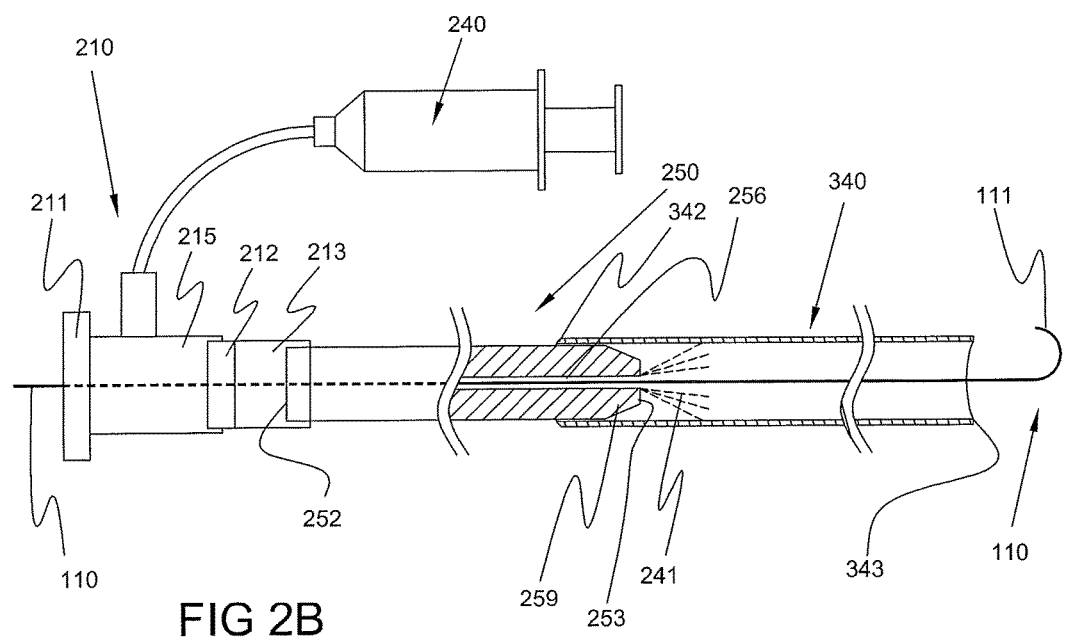

Referring now to FIGS. 2A and 2B, side partial sectional views of an insertion device, and a method of using the insertion device to insert a mandrel into a tubular member, are illustrated. Referring specifically to FIG. 2A, insertion device 210 includes a fluid delivery source, syringe 240, which is fluidly attached to valve assembly 215. In an alternative embodiment, a different fluid delivery source is provided such as a fluid source including but not limited to: a gravity driven fluid source such as a collapsible fluid bag placed at a location above mandrel 250; and fluid pumping means such as a syringe pump, a displacement pump or a peristaltic pump. The fluid delivery source can be constructed and arranged to deliver fluid at a constant flow or at a constant pressure, such as a pressure approximating a patient's arterial pressure, including both the patient's systolic and diastolic pressures. Valve assembly 215 is typically a touhy-borst or other valve assembly configured to limit fluid transfer past one or more shafts passing through valve assembly 215. Flange 211 is a valve controller designed to be rotated to adjust the sealing diameter of valve assembly 215. Tubing 213, which can comprise flexible or rigid tubing, is attached to connecting portion 212 of valve assembly 215, such as via adhesive or a removable attachment mechanism. Mandrel 250 can be attached to tubing 213, such that mandrel end 252 is positioned within tubing 213 and forms a relatively tight fluid seal.

Mandrel 250 includes lumen 256 which travels from mandrel end 252 to end 253. Mandrel end 253 includes bevel 259, configured to provide atraumatic insertion of mandrel end 253 into conduit 340. Conduit 340 includes ends 342 and 343. A guidewire, J-tipped guidewire 110, can be inserted through lumen 256 and can travel proximally through valve assembly 215. Guidewire 110 typically has the construction of a standard interventional guidewire and includes a soft, flexible tip configured for atraumatic insertion and advancement through the lumen of a blood vessel. Guidewire 110 can include one or more coatings such as a lubricous coating, including but not limited to, a lubricous polymer coating. Flange 211 can be rotated such that valve assembly 215 provides a relatively tight fluid seal around guidewire 110 such that fluid introduced by syringe 240 into valve assembly 215 does not pass beyond (i.e. as shown on the page to the left of) flange 211. The J-tipped end 111 of guidewire 110 can be passed through end 342 of conduit 340. J-tipped end 111 and other end portions of guidewire 110 are designed to be soft, flexible, and free from sharp edges such as to reduce trauma while being inserted into a blood vessel, other living tissue, or other tubular materials that can be susceptible to damage. Mandrel end 253 is positioned to be inserted into end 342 of conduit 340, while fluid 241, supplied by syringe 240, exits lumen 256 and enters into conduit 340, as shown, In one embodiment, conduit 340 comprises a segment of harvested vein and fluid is delivered in the same direction of the venous flow that was present prior to harvesting. Fluid 241, typically saline or other biocompatible fluid, and/or a fluid including one or more lubricants such as silicone gel, can be used to reduce friction, stress, strain, tearing and other undesired forces that can occur during insertion of mandrel 250 into conduit 340. Fluid 241 can comprise a conductive fluid such as fluid configured to be charge or otherwise placed at an electrical potential to support an electrospinning process. Fluid 241 can include one or more drugs, cells or other agents, such as an agent configured to improve the long term patency of the graft device and described in detail hereabove. Fluid 241 can be configured and/or delivered to hydrate conduit 340.

Referring now specifically to FIG. 2B, mandrel second end 253 can be partially inserted into conduit 340 through end 342. As fluid 241 continues to be delivered, continuously or in discrete bursts, mandrel end 253 can be advanced until it exits the opposite end 343 of conduit 340. In subsequent steps, conduit 340 can be advanced such that mandrel ends 252 and 253 protrude beyond conduit ends 342 and 343, respectively. Insertion device 210 is removed, such that mandrel ends 252 and 253 can be inserted into a rotational drive of into an electrospinning unit, as has been described in detail in reference to FIG. 1 hereabove. One or both of mandrel ends 252 and 253 can include a mating element, such as a recess or a projection, such as to engage a motor shaft portion of a rotational drive.

Referring now to FIGS. 3A and 3B, side partial sectional views of a removal device, and a method of using the removal device to remove a mandrel from a tubular member and/or a graft device of the present invention, are illustrated. Referring specifically to FIG. 3A, removal device 310 includes a fluid delivery source, syringe 240, which is fluidly attached to valve assembly 315. In an alternative embodiment, a different fluid delivery source such as a gravity fed or pump driven fluid source is provided. Valve assembly 315 is typically a touhy-borst construction or other valve assembly configured to limit fluid transfer past one or more shafts passing through valve assembly 315, and can be similar to valve assembly 215 of FIGS. 2A and 2B. Flange 311 is a valve controller, attached to a first end of valve assembly 315 and designed to be rotated to adjust the sealing diameter of valve assembly 315. Attached to the other end of valve assembly 315 is shaft 317, typically a thin walled tube with beveled distal end 316. Shaft 317 typically has a wall thickness less than about 0.100 inches, more typically less than about 0.020 inches. Shaft 317 can be configured to maintain an opening in the end of conduit 340. Shaft 317 can be configured to frictionally engage conduit 340, such as when shaft 317 includes one or more adhesives or roughened surfaces. Shaft 317 can have a beveled end 316.

Mandrel 250 includes lumen 256 which travels from mandrel end 252 to end 253, either or both ends 252 and 253 including beveled ends as shown. Alternatively or additionally, lumen 256 can exit the outer surface (i.e. side) of mandrel 250, such as through an exit hole, not shown. Mandrel 250 can be inserted into conduit 340, through end 342, such as via the method described in reference to FIG. 1 or 2A and 2B described hereabove. Mandrel 250 can be inserted into conduit 340 using a guidewire, not shown, but placed within lumen 256.

Referring specifically to FIG. 3B, beveled end 316 and the walls of shaft 317, each of removal device 310, can be inserted between graft device 100 and the outer surface of mandrel 250, first passing over mandrel beveled end 252. During insertion, fluid can be delivered through shaft 317, such as with flange 311 closed to form a seal (i.e. little or no fluid passing through valve assembly 315). As end 252 of mandrel 250 entered valve assembly 315, flange 311 can be rotated to accommodate the diameter of mandrel 250, thus allowing it to pass through valve assembly 315 and flange 311 as shown in FIG. 3B. Flange 311 can be selectively tightened to reduce fluid passage around mandrel 250, and loosened to allow motion of mandrel 250 through valve assembly 315. As oriented on the page, device 100 is removed from mandrel 250 by advancing removal device 310 to the right, advancing mandrel 250 to the left, and/or advancing graft device 100 to the right. During the removal process, fluid 241, comprising saline or other friction reducing fluid, can be delivered, via fluid lumen 357, between device 100 and the outer surface of mandrel 250. After removal of mandrel 250, device 100 can be implanted in the patient, such as in a cardiac or other bypass procedure. Alternatively or additionally, removal device 310 can be configured as an insertion device, constructed and arranged to atraumatically insert mandrel 250 into conduit 340 and/or graft device 100.

Figure 4A:
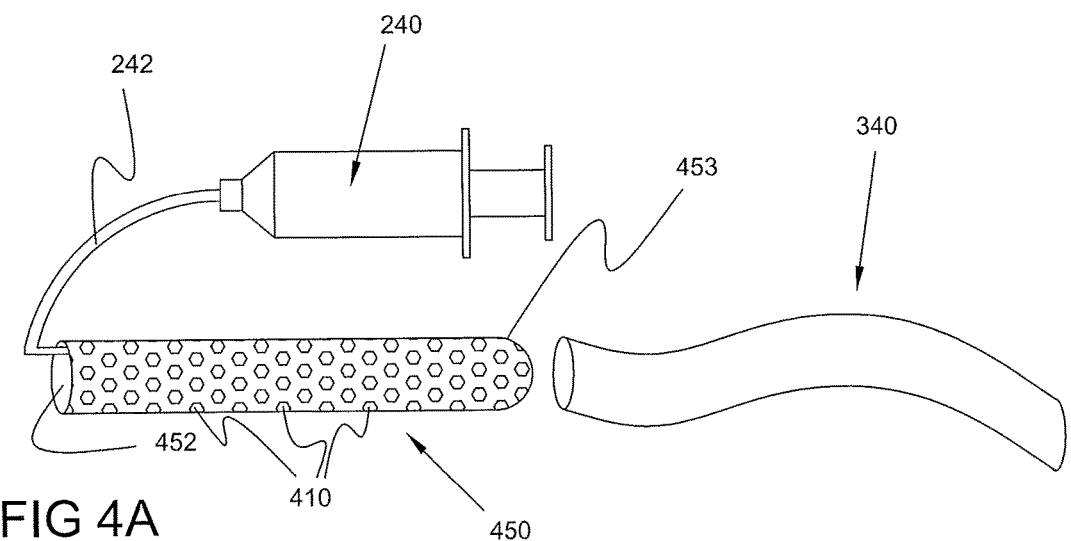
FIGS. 4A and 4B illustrate side views of an exemplary porous mandrel comprising side holes, shown prior to and during insertion, respectively.
Figure 4B:
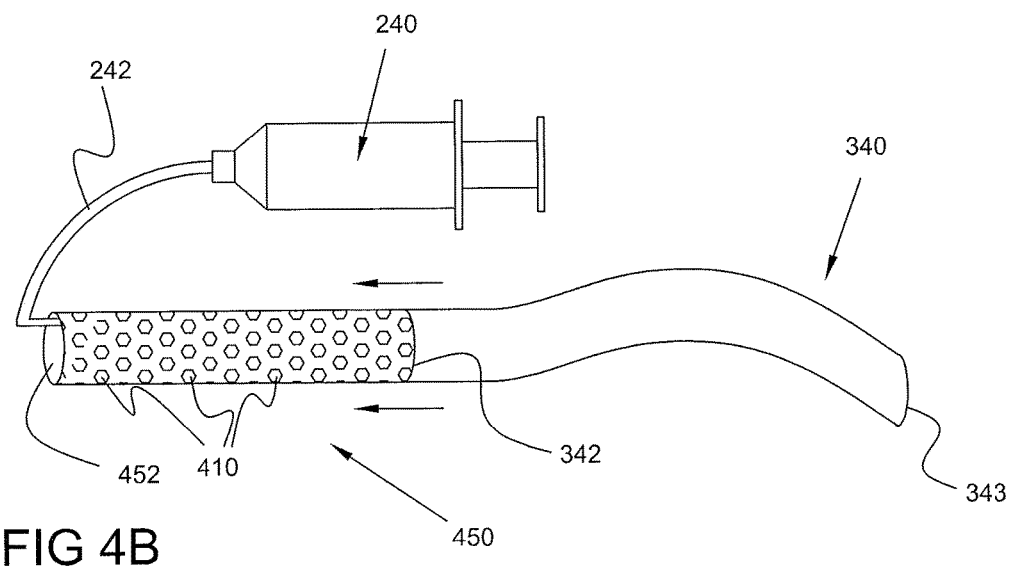

Referring now to FIGS. 4A and 4B, side views of a porous mandrel comprising side holes, depicted prior to and during insertion, respectively, are illustrated. Mandrel 450 comprises a first end 452 and a second end 453. End 453 comprises a rounded tip, such as a tip comprising a full radius. Mandrel 450 is fluidly attached to a fluid delivery system, syringe 240. Alternatively, a fluid pumping system can be used as has been described hereabove. Syringe 240 includes tubing 242 which is in fluid communication with one or more side holes 410 of mandrel 450. Side holes 410 can be equally spaced, such as in radially and/or longitudinally equidistantly spaced matrix of holes. Side holes 410 can be in fluid communication with porous material of mandrel 450, and/or side holes 410 can be attached to a series of interconnected lumens in fluid communication with tubing 242. Fluid, such as a friction reducing fluid or other flowable material, can be delivered through side holes 410 manually or automatically, such that insertion of mandrel 450 into conduit 340 is made less traumatic to conduit 340. Alternatively or additionally, fluid can be delivered to hydrate conduit 340 and/or to deliver one or more agents to conduit 340, as has been described in detail hereabove.

Referring specifically to FIG. 4B, end 342 of conduit 340 has been partially placed over mandrel 450, starting at, for example, mandrel end 453 of FIG. 4A, and advancing conduit 340 in the direction shown. During the placement, fluid can be delivered through side holes 410 as described above. In an alternative embodiment, end 452 of mandrel 450 is partially inserted into conduit 340, starting at conduit end 342 and advancing mandrel 450 in a direction opposite to that shown in FIG. 4B, typically while fluid is delivered through side holes 410. In subsequent steps, conduit 340 and/or mandrel 450 can be advanced such that mandrel ends 452 and 453 extend beyond the ends 342 and 343 of conduit 340, such that ends 452 and 453 are positioned to be inserted into a rotational drive of into an electrospinning unit, as has been described in detail in reference to FIG. 1 hereabove.

One or both of mandrel ends 452 and 453 can include a mating element, such as a recess or a projection, such as to engage a motor shaft portion of a rotational drive.

Referring now to FIGS. 5A through 5D, a sequence of side views of a guidewire tipped solid core mandrel, in multiple steps of insertion into a tubular member, are illustrated. Mandrel 550 comprises solid shaft 551 with a first end 552 and tapered second end 553. Attached to tapered end 553 is a guidewire 557, typically a flexible guidewire of similar construction to the interventional guidewire construction described hereabove. Tapered end 553 and guidewire 557 are configured to allow atraumatic insertion of mandrel 550 into a tubular member such as a saphenous vein segment or other conduit. Mandrel 550 includes a breakaway location, score mark 555, configured to allow guidewire 557 and distal end to be removed when a force is applied proximate score mark 555. Alternative to score mark 555, end 553 and guidewire 557 can be removably attached to shaft 551, such as with an attachment comprising: threads; a frictionally engaging surface; a snap fit; a groove; a recess; and combinations of these.

Referring specifically to FIG. 5B, guidewire 557 and tapered end 553 of mandrel 550 can be slidingly advanced into conduit end 342, and part way through conduit 340. In FIG. 5C, tapered end 553 can exit the opposite end 343 of conduit 340. In FIG. 5D, tapered end 553 and guidewire 557 can be removed after a force having been applied at score mark 555, creating a new mandrel end 553'. Either or both ends 552 and 553' can include engagement means, not shown but configured to engage with a support and/or a rotational drive element such as the shaft of a motor. Circumferential clips 561a and 561b can be placed around tubular member 340, such as to maintain the position of tubular member 340 relative to mandrel 550 during the electrospinning process to follow. Clips 561a and 561b can comprise clips selected from the group consisting of: a spring clip; a tubing clamp; a compression ring; a tie wrap; and combinations of these.

Figure 6:
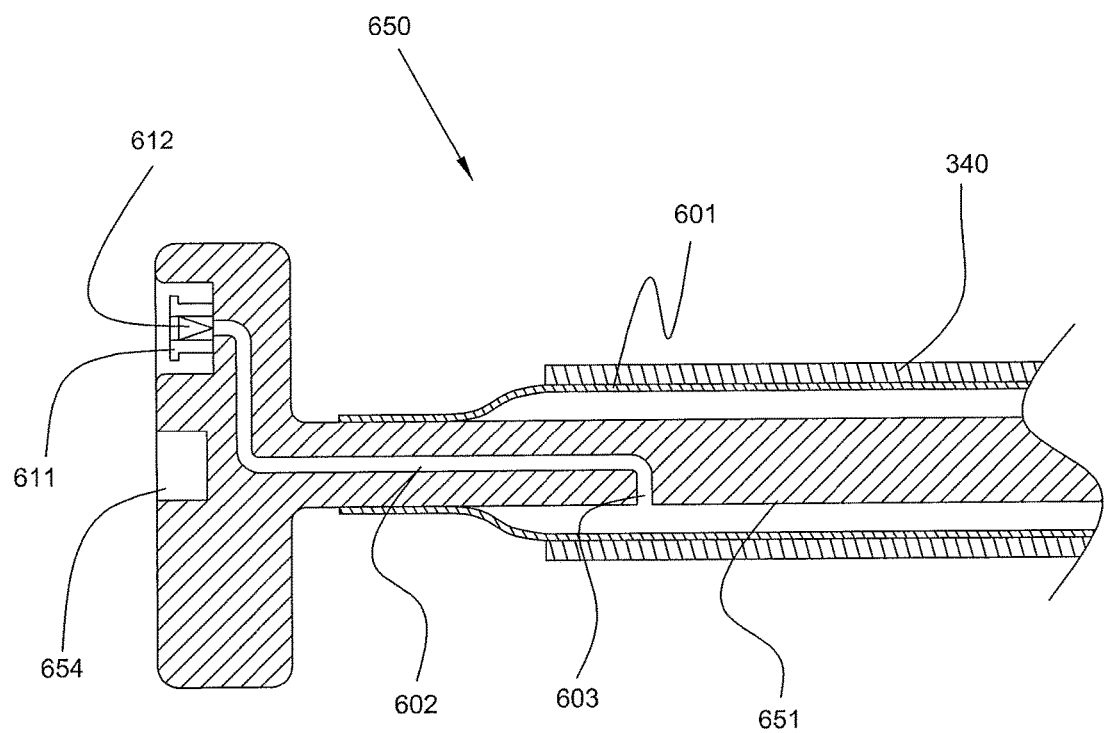
FIG. 6 illustrates a side sectional view of an exemplary mandrel comprising a surrounding balloon.

Referring now to FIG. 6, a side sectional view of a mandrel comprising a surrounding balloon is illustrated. Mandrel 650 comprises shaft 651 and a surrounding balloon 601. Balloon 601 is shown in an inflated, radially expanded state, such that its diameter approximates the inner diameter of conduit 340 into which mandrel 650 has been inserted. In this configuration, an applied fiber matrix can have a relaxed inner diameter that approximates the relaxed outer diameter of conduit 340, such that a restrictive force will begin to be applied as conduit 340 begins to expand (e.g. an expansion that occurs when exposed to arterial pressure). In an alternative embodiment, balloon 601 diameter is less than the inner diameter of conduit 340, such that conduit 340 can loosely surround mandrel 650 and a subsequently applied fiber matrix can provide a radially constrictive force as conduit 340 is pressurized to approach its previous inner diameter. In another alternative embodiment, balloon diameter 601 is greater than the inner diameter of conduit 340, such that conduit 340 can be expanded by mandrel 650, and a subsequently applied fiber matrix will not apply a radially constrictive force until conduit 340 is pressurized to a diameter greater than its previous inner diameter.

Balloon 601 can comprise a diameter that is relatively uniform along its length, or of varied diameter. Multiple balloons can be included along shaft 651, such as multiple balloons with similar or dissimilar properties or performance. Balloon 601 can be constructed and arranged to deliver one or more fluids through its surface, or a portion of its surface, such as when balloon 601 comprises a weeping balloon.

Mandrel 650 can be inserted into conduit 340 at conduit end 342 in a deflated or partially deflated state. In one embodiment, balloon 601 is sized to approximate the diameter of shaft 651 of mandrel 650 when balloon 601 is deflated. In another embodiment, balloon 601 is sized to have a diameter less than the diameter of shaft 651 such that balloon 601 tightly surrounds shaft 651 when balloon 601 is deflated. Balloon 601 can be a compliant or non-complaint balloon, such as a non-compliant balloon configured to expand to a diameter less than, equal to, or greater than the inner diameter of conduit 340. Balloon 601 can include one or more coatings, such as a hydrophobic coating, a hydrophilic coating and/or a lubricous coating such as a lubricious polymer coating. Mandrel 650 includes an inflation port comprising connector 611, typically a luer connector configured to attach to a fluid delivery device, such as a syringe, gravity feed or pump device, as has been described hereabove. A valve, such as duck bill valve 612 can be included, such as to maintain pressure in balloon 601 after inflation. Fluid passing through connector 611 passes through lumen 602 and exits hole 603, and enters the area between shaft 651 and balloon 601. Mandrel 650, with conduit 340 surrounding and balloon 601 inflated, is ready for insertion in fiber application device such as electrospinning unit 100 of FIG. 1. Mandrel 650 includes recess 654 which is configured to operably connect to a rotational drive, such as a motor shaft. Recess 654 can be configured to frictionally engage a rotational drive, and can include a snap fit connection. Recess 654 can include one or more surfaces that interlock with a motor shaft, such as to create a keyed connection. After a fiber matrix has been applied to conduit 340, balloon 601 can be deflated, such as by applying a vacuum to connector 611, and mandrel 650 removed from conduit 340.

Figure 7:
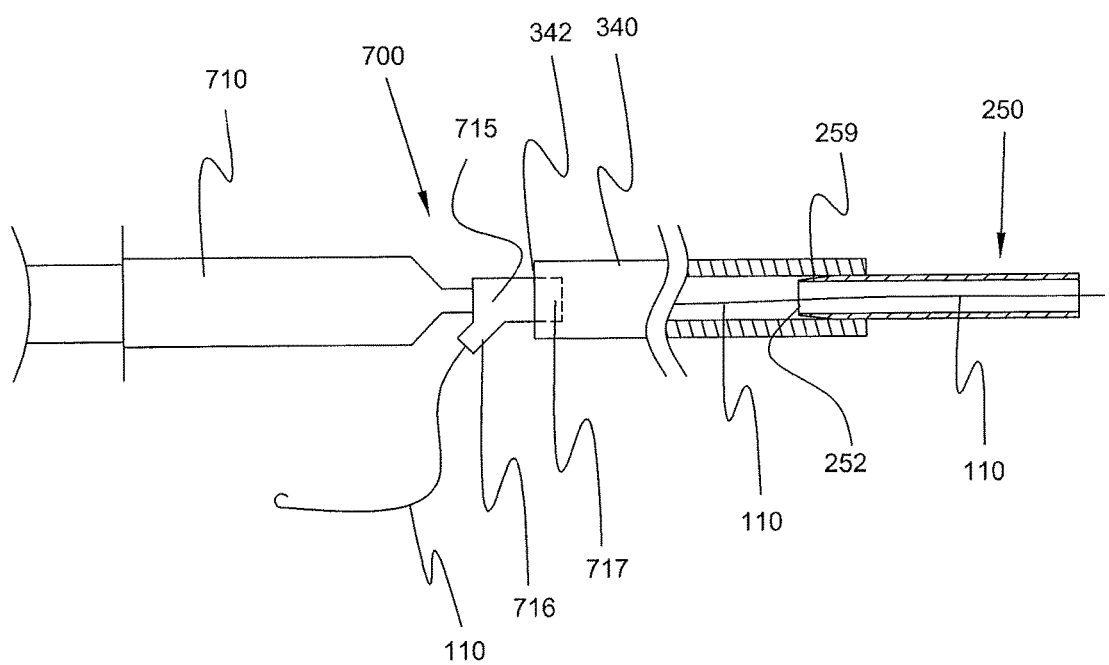
FIG. 7 illustrates a side partial sectional view of an exemplary introducer device and mandrel, inserted into opposite ends of a tubular member.

Referring now to FIG. 7, a side partial sectional view of an introducer device and mandrel, inserted into opposite ends of a tubular member, is illustrated. Introducer device 700 includes valve assembly 715, such as a touhy-borst valve assembly described hereabove. Valve assembly 715 is attached to syringe 710, such that fluid delivered from syringe 710 exits distal end 717 of valve assembly 715. Valve assembly 715 includes an exit port 716 such that one or more shafts can pass through valve assembly 715 and through exit port 716, typically passing through a sealed or sealable orifice such as with a touhy-borst valve assembly. Introducer device 700 is shown in FIG. 7 inserted into end 342 of conduit 340.

Mandrel 250, including end 252 with bevel 259, can be placed over guidewire 110. Guidewire 110 can be threaded through conduit 340, and then through introducer device 700 exiting through exit port 716. Introducer device 700 includes one or more valve controls, such as a rotating knob, not shown, such that valve assembly 715 can form a fluid seal around guidewire 110. In a preferred method, fluid is introduced from syringe 710, through valve assembly 715 and into conduit 340 as mandrel 250 is atraumatically advanced over guidewire 110 and into conduit 340.

Figure 8A:
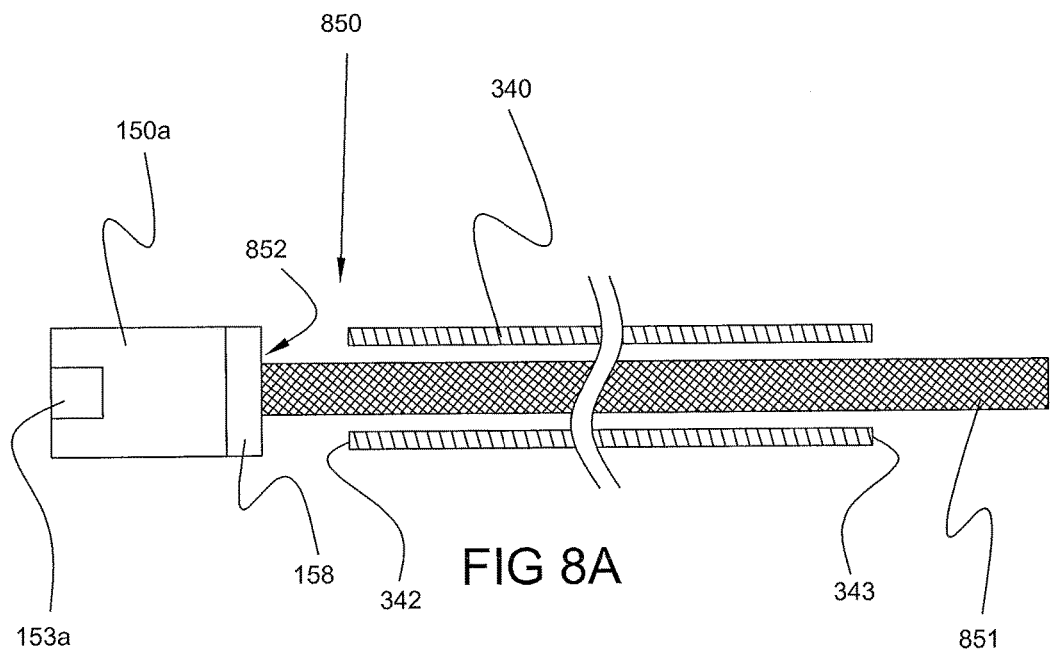
FIGS. 8A and 8B illustrate side sectional views of an exemplary mandrel comprising a braided construction, in compressed and expanded states, respectively.
Figure 8B:
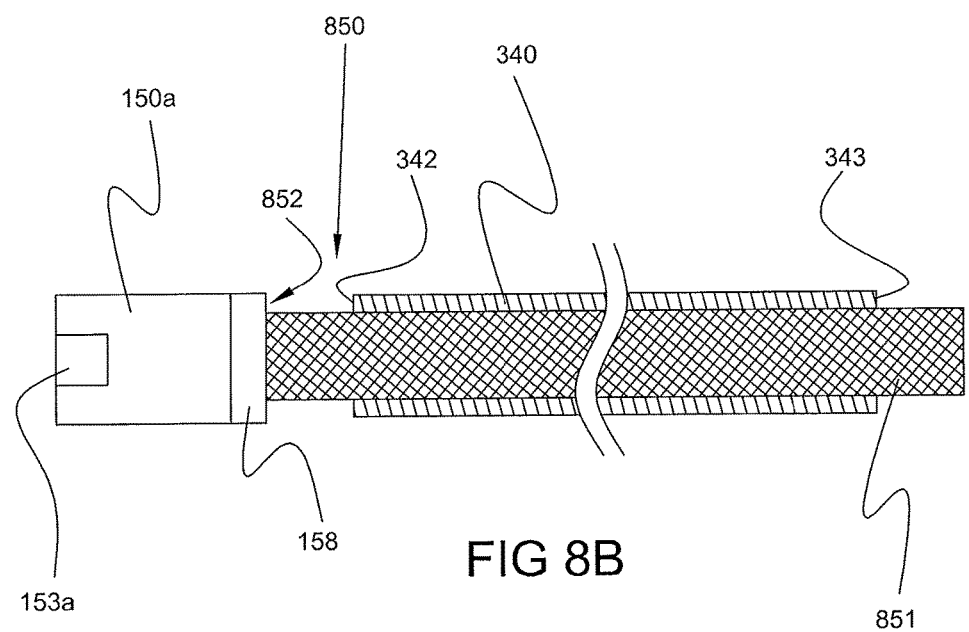

Referring now to FIGS. 8A and 8B, side sectional views of a mandrel comprising a braided construction, in compressed and expanded states, respectively, are illustrated. Mandrel 850 comprises shaft 851, a braided construction of multiple filaments such as multiple metal filaments. In one embodiment, shaft 851 comprises a braid of stainless steel filaments or other metallic materials such Nitinol, other titanium alloys, cobalt-chrome alloys, and magnesium alloys. Shaft 851 is constructed and arranged to radially compress when longitudinally elongated, such as to the longitudinally elongated, radially compressed state shown in FIG. 8A. When radially compressed, mandrel 850 can be atraumatically inserted into conduit 340, through conduit ends 342 or 343. The insertion can be performed over an integral or separate guidewire, not shown but as has been described hereabove. Support 150a is placed on proximal end 852 of mandrel 850. Support 150a includes circumferential clamp 158 configured to engage the end of a braided shaft. Support 150a also includes slot 153a, configured to mate with a rotational drive, such as a motor shaft of FIG. 1.

In FIG. 8B, shaft 851 has been shortened (e.g. longitudinally compressed), causing shaft 851 to radially expand to approximate the inner diameter of conduit 340. Support 150a and circumferential clamp 158 can be adjusted such as to lock or otherwise prevent changing of the diameter of shaft 851. A second support, not shown but of similar or dissimilar construction to support 150a, can be similarly applied to end 852 of mandrel 850, such that mandrel 850 can be inserted into a fiber delivery assembly, such as electrospinning unit 100 of FIG. 1. Prior to electrospinning, shaft 851 can be expanded to a diameter less than, approximately equal to, or greater than a relaxed (i.e. no forces exerted) diameter of conduit 340.

As described in reference to FIG. 6 hereabove, the diameter of the applied fiber matrix can be adjusted by controlling the diameter of a mandrel shaft during the electrospinning process. For mandrel 850 of FIG. 8, shaft 851 diameter can be set (e.g. by longitudinally elongating or compressing shaft 851) to determine how and when restrictive forces are applied to conduit 340 by the fiber matrix as conduit 340 is expanded, such as when expanded by exposure to arterial blood pressure.

Figure 9A:
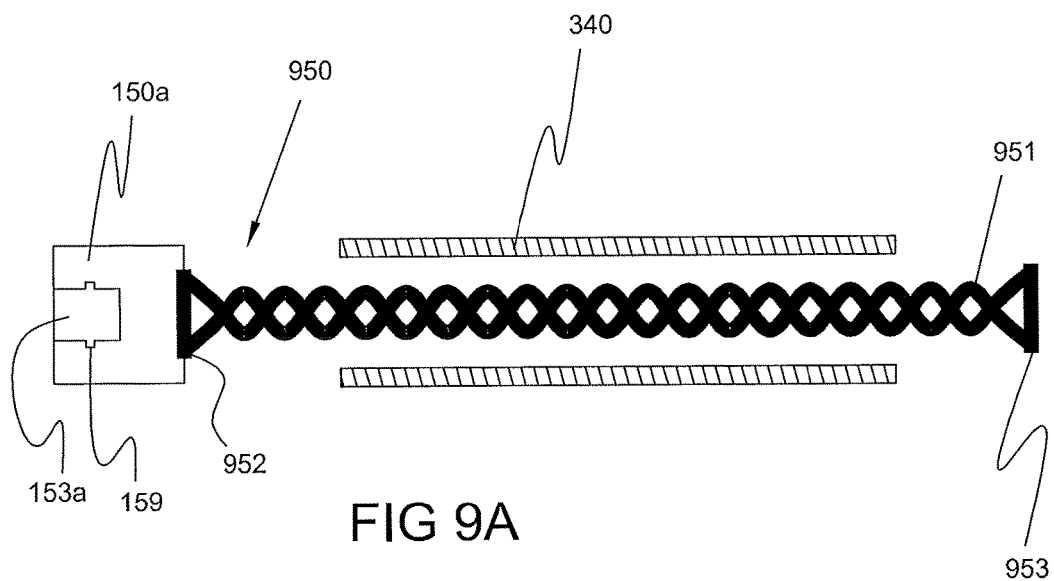
FIGS. 9A and 9B illustrate side sectional views of an exemplary mandrel comprising a helical construction, in compressed and expanded states, respectively.
Figure 9B:
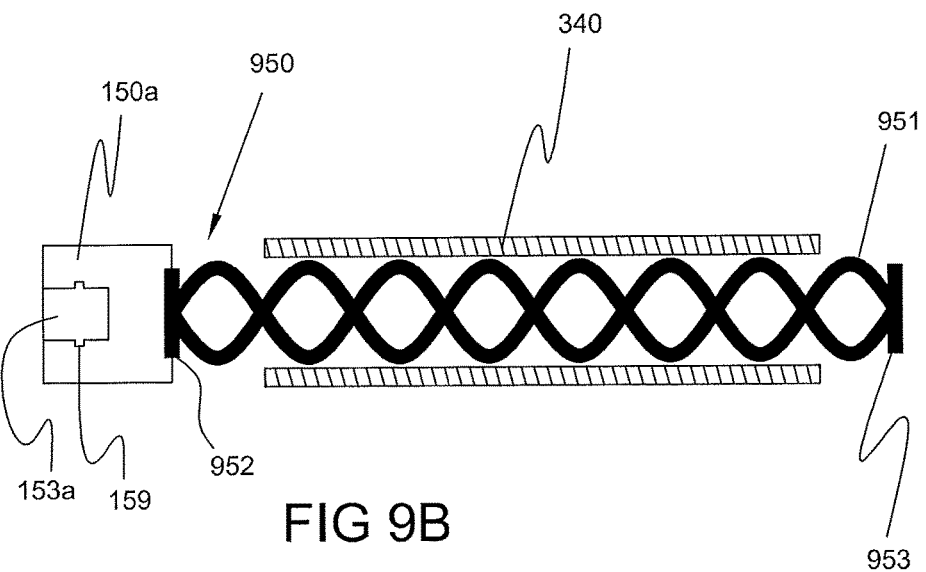

Referring now to FIGS. 9A and 9B, side sectional views of a mandrel comprising a helical construction, in radially compressed and radially expanded states, respectively, are illustrated. Mandrel 950 comprises shaft 951, a double helix construction of two ribbons or other filaments, such as multiple metal filaments. In one embodiment, shaft 951 comprises a helix of shaped memory or superelastic metal material such as Nitinol. Shaft 951 is constructed and arranged to radially compress when longitudinally elongated, such as to the longitudinally elongated, radially compressed state shown in FIG. 9A. When radially compressed, mandrel 950 can be atraumatically inserted into conduit 340. A support 150a is placed on proximal end 952 of mandrel 950. Support 150a is attached to end 952 of mandrel 950. Support 150a also includes slot 153a, configured to mate with rotational drive means, such as the rotational drive means of FIG. 1. Slot 153a includes groove 159, configured to further engage rotational drive means, such as when the rotational drive means comprises a shaft with a radially extending spring-pin or piston configured to mate with groove 159.

Referring to FIG. 9B, shaft 951 can been shortened (i.e. longitudinally compressed), causing shaft 951 to radially expand to approximate the inner diameter of conduit 340. A second support can be attached to end 953 of shaft 951, second support not shown but of similar or dissimilar construction to support 150a. Mandrel 950 can be positioned in a fiber application unit, such that shaft 951's length is fixed to maintain the radially expanded state of FIG. 9B. Typical fiber application units can be similar to electrospinning unit 100 of FIG. 1.

As described in reference to FIG. 6 hereabove, the diameter of the applied fiber matrix can be adjusted by controlling the diameter of a mandrel shaft during the electrospinning process. For mandrel 950 of FIG. 9, shaft 951 diameter can be set (e.g. by longitudinally elongating or compressing shaft 951) to determine how and when restrictive forces are applied to conduit 340 by the fiber matrix as conduit 340 is expanded, such as when expanded by exposure to arterial blood pressure.

Figure 10A:
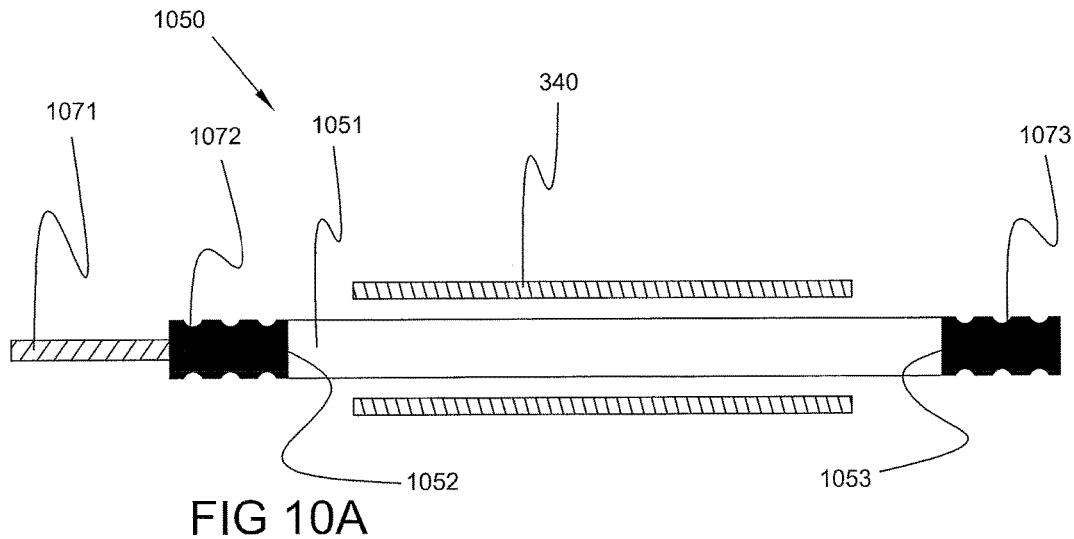
FIGS. 10A and 10B illustrate side sectional views of an exemplary mandrel comprising a tube configured to radially expand under longitudinal compression, in compressed and expanded states, respectively.
Figure 10B:
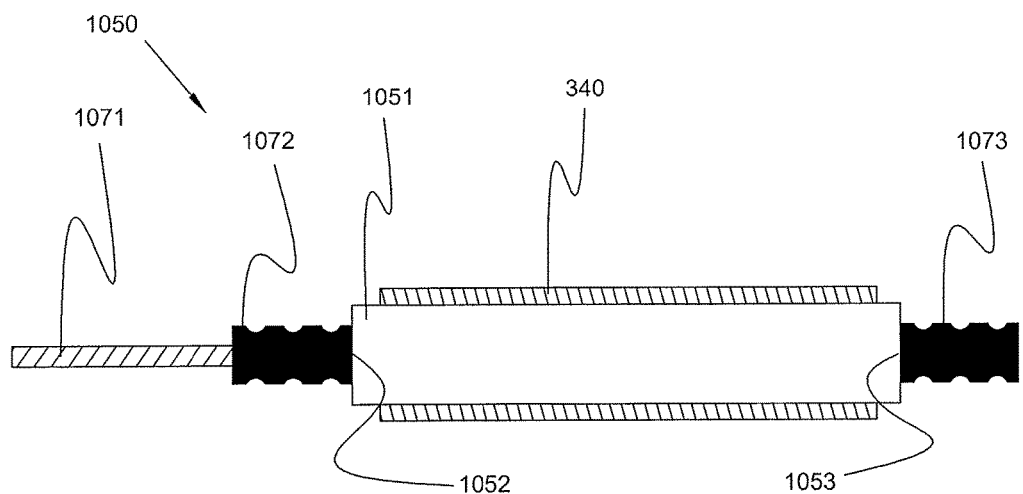

Referring now to FIGS. 10A and 10B, side sectional views of a mandrel comprising a longitudinally compressible tube, in compressed and expanded states, respectively, are illustrated. Mandrel 1050 comprises shaft 1051, a compressible tube such as an elastomeric tube. Shaft 1051 is constructed and arranged to radially expand when longitudinally compressed, such as to the longitudinally compressed, radially expanded state shown in FIG. 10B. Prior to longitudinal compression and radial expansion, mandrel 1050 can be atraumatically inserted into conduit 340, as is shown in FIG. 10A.

Mandrel 1050 includes threaded rod 1071 which is slidingly received by a lumen of shaft 1051, lumen not shown but typically approximating or slightly larger than the diameter of threaded rod 1071. Nuts 1072 and 1073 are threadingly engaged with rod 1072 and positioned at ends 1052 and 1053 of shaft 1051. A metal plate such as a washer, not shown, can be positioned between nut 1072 or 1073, such as to distribute forces along the surface of end 1052 or 1053, respectively. Nut 1072, configured such that it translates to the right (on the page) when rotated clockwise, causes shaft 1051 to longitudinally compress, and radially elongate. Alternatively or additionally, nut 1073, configured such that it translates to the left (on the page) when rotated clockwise, also causes shaft 1051 to longitudinally compress and radially expand. Opposite rotation (e.g. counter-clockwise) of either nut 1072 or 1073 causes shaft 1051 to longitudinally elongate and radially compress. Rotation of nuts 1072 and/or 1073 can be used to radially compress shaft 1051, such as to the state shown in FIG. 10A. In this radially compressed condition, the diameter of shaft 1051 is less than the inner diameter of conduit 340 allowing atraumatic insertion of mandrel 1050 into conduit 340. Rotation of nuts 1072 and/or 1073 can also be used to radially expand shaft 1051, such as to the state shown in FIG. 10B. In this radially expanded condition, the diameter of shaft 1051 approximates the inner diameter of conduit 340 allowing support of mandrel 1050 to conduit 340, such as to provide support during application of a fiber matrix.

In one embodiment, nuts 1072 and 1073 are configured to operably engage rotational drive means, such as the rotational drive means described in reference to FIG. 1 hereabove. Alternatively, one or more support or other engagement means can attach to threaded rod 1071, nut 1073 and/or nut 1073, not shown but also configured to attach to rotational drive means.

As described in reference to FIG. 6 hereabove, the diameter of the applied fiber matrix can be adjusted by controlling the diameter of a mandrel shaft during the electrospinning process. For mandrel 1050 of FIGS. 10A and 10B, shaft 1051 diameter can be set (e.g. by rotating nut 1072 and/or nut 1073) to determine how and when restrictive forces are applied to conduit 340 by the fiber matrix as conduit 340 is expanded, such as when expanded by exposure to arterial blood pressure.

Figure 11A:
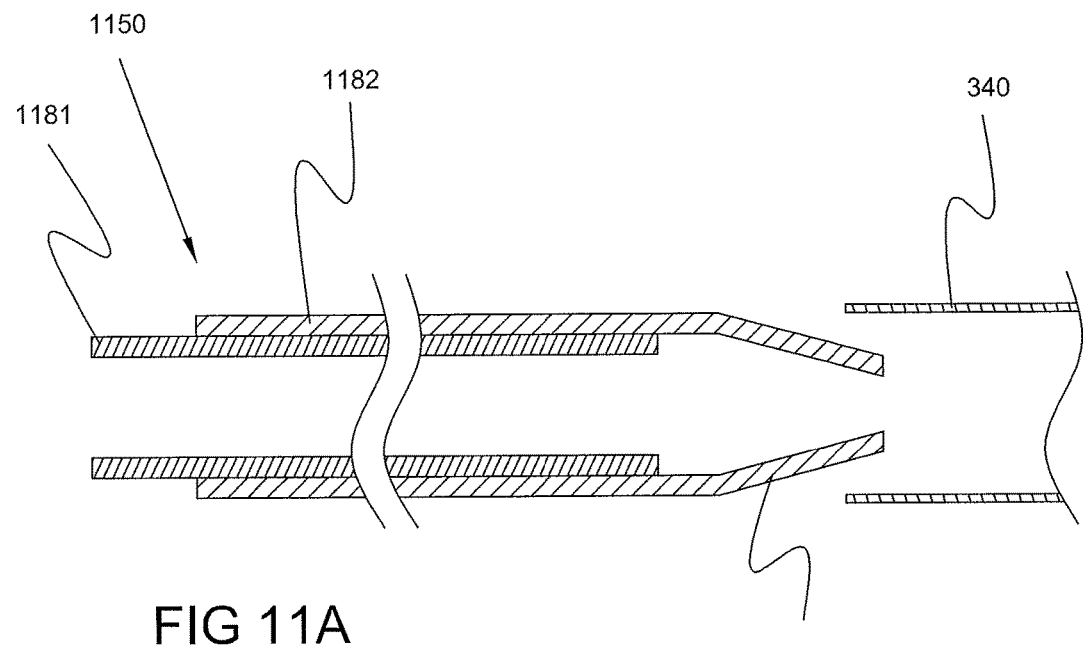
FIGS. 11A and 11B illustrate side sectional views of an exemplary mandrel comprising a two-pieced construction, prior to and after partial insertion into a tubular member, respectively.
Figure 11B:
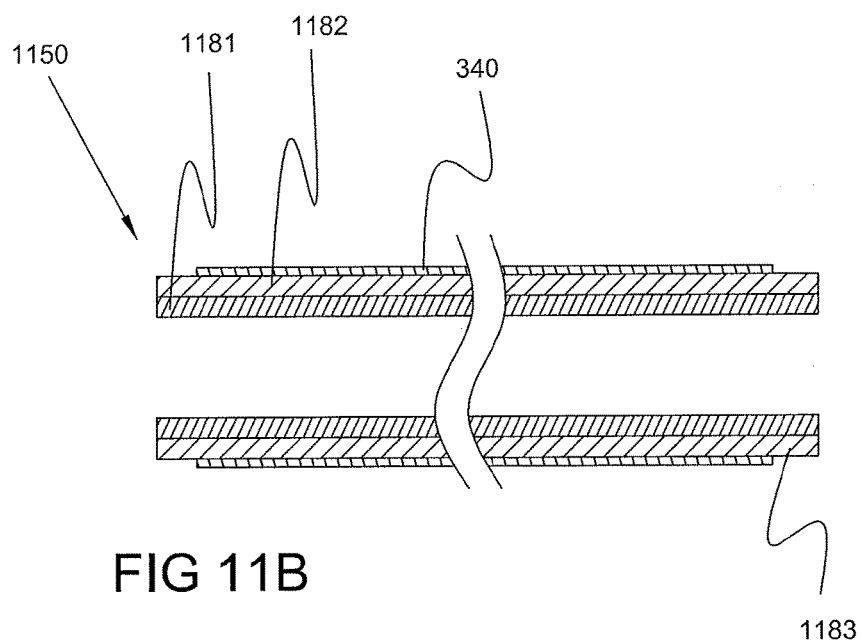

Referring now to FIGS. 11A and 11B, side sectional views of a mandrel comprising a two-pieced construction, prior to and after partial insertion into a tubular member, respectively, is illustrated. Mandrel 1150 includes inner tube 1181 and outer tube 1182. Outer tube 1182 includes a tapered distal end 1183, such as a resiliently biased tapered end configured for atraumatic insertion into conduit 340. Outer tube 1182 can be made of a thinner and/or softer material than inner tube 1181, such as to further reduce trauma as tapered end 1183 is advanced into conduit 340.

Referring specifically to FIG. 11B, mandrel 1150 can be inserted into conduit 340 and inner tube 1181 advanced, to the right (on the page), causing the tapered end 1183 of outer tube 1182 to straighten. Mandrel 1150 and conduit 340 can then be inserted into a fiber application unit to generate a graft device of the present invention.

In one embodiment, inner tube 1181 is constructed of a rigid material, such as a material rigid enough to support a fiber application process such as the electrospinning process described in reference to FIG. 1 hereabove. Alternatively or additionally, outer tube 1182 can be collapsible, with inner tube 1181 configured to be more rigid such as to prevent collapse. Alternative to the tapered end 1183 of outer tube 1182, a portion of outer tube 1182 can be collapsible, such as a portion that is collapsed when inner tube 1181 does not reside with that portion. In this particular embodiment, the collapsed portion of outer tube 1182 can be atraumatically introduced into conduit 340. Numerous other configurations of inner and outer tubes, such as slidingly engaged inner and outer tubes with similar or dissimilar properties, can be used to minimize the trauma caused by insertion of a mandrel into a tubular member. One or both ends of the inner 1181 and/or outer 1182 tubes can include a reduced diameter, a taper or bevel, a rounded tip, or other atraumatic feature.

Figure 12A:
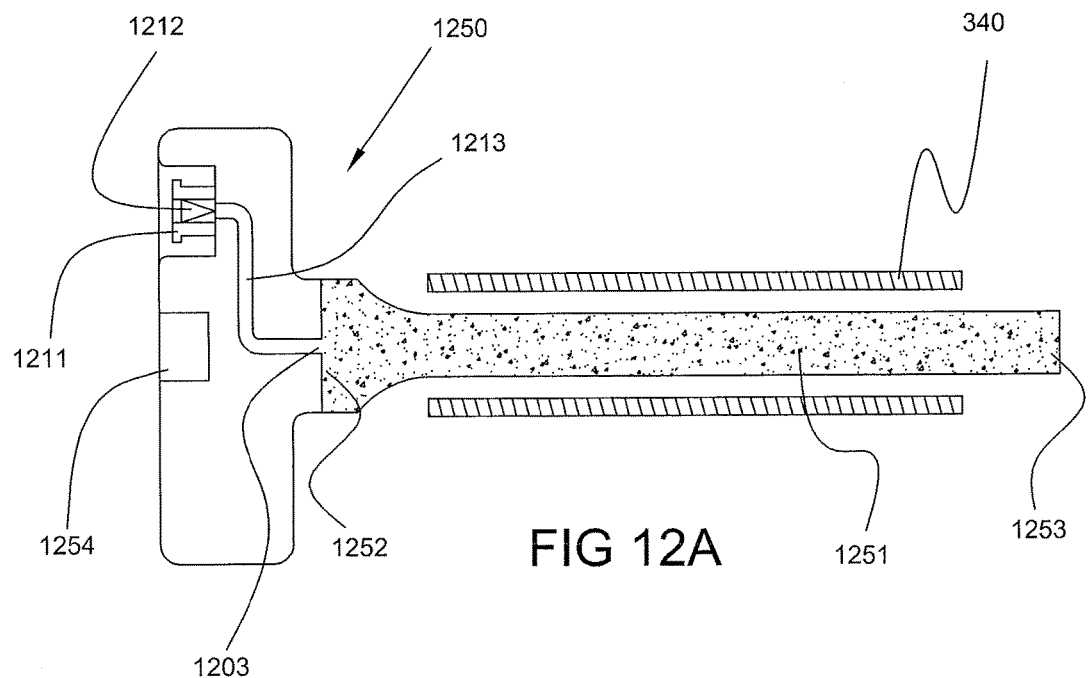
FIGS. 12A and 12B illustrate side sectional views of an exemplary mandrel comprising a liquidly expandable construction, in compressed and radially expanded states, respectively.
Figure 12B:
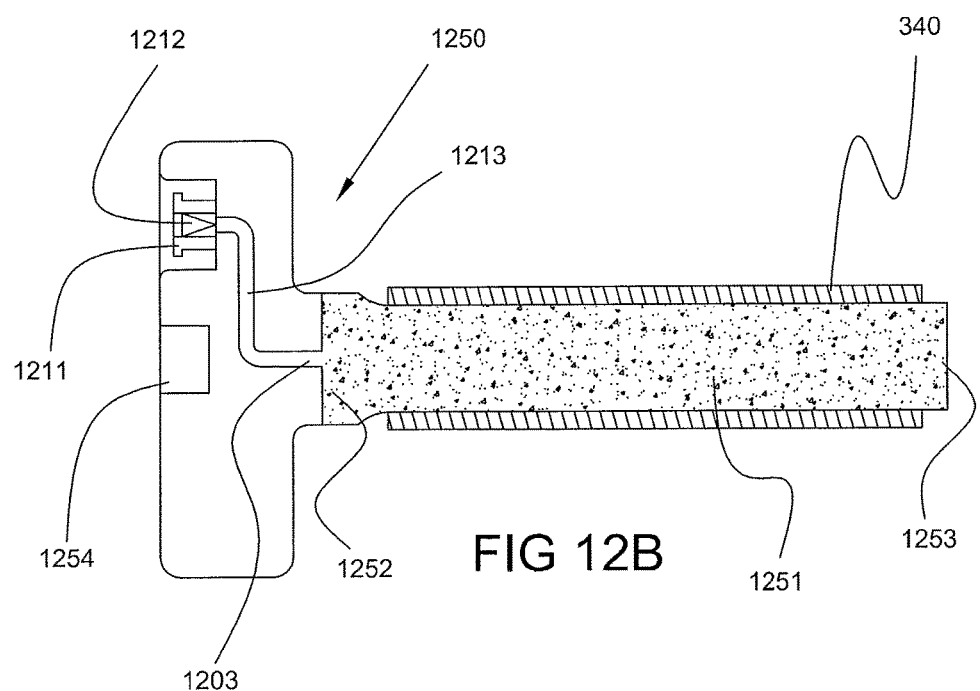

Referring now to FIGS. 12A and 12B, side sectional views of a mandrel comprising a fluidly expandable shaft, in compressed and radially expanded states, respectively, are illustrated. Mandrel 1250 comprises an expandable shaft 1251, with ends 1252 and 1253 and constructed of a sponge-like material (e.g. semi-permeable membranes regulating the flow of water), and thus the expansion of the expandable mandrel by osmotic or oncotic mechanisms, or other material configured to expand or shrink when exposed to a fluid. In one non-limiting embodiment, a liquid (e.g. saline; a more viscous Newtonian fluid such as glycerin or solutions of dextran in saline; a non-Newtonian fluid such as a hydrogel; and/or suspensions of particulates) can be manually infused into expandable shaft 1251. The amount of fluid infused or withdrawn into or from the system can determine the size of the expandable shaft 1251. The fluid used to expand and/or shrink the expandable shaft 1251 can be a gas such as air, or an inert gas such as nitrogen, or helium. In another non limiting example, expandable shaft 1251 can be configured as an osmotic or oncotic pump. In this embodiment, after the correct amount of fluid solution or suspension (e.g. with the correct osmolarity or oncotic pressure) is infused into the expandable shaft 1251, expandable shaft 1251 can expand to the desired level, while simultaneously generating slow and controlled transmural permeation of moieties providing both protective lubrication and hydration to conduit 340.

Referring specifically to FIG. 12A, shaft 1251 is shown in an unexpanded state, such that its diameter is less than the inner diameter of conduit 340 such that end 1253 of shaft 1251 can be atraumatically inserted into conduit 340. Mandrel 1250 includes a fluid delivery port comprising connector 1211, typically a luer connector configured to attachment to a fluid delivery device, not shown but typically a syringe or pump device, as has been described hereabove. A valve, such as duck bill valve 1212 can be included, such as to maintain pressure in shaft 1251 after radial expansion. Fluid passing through connector 1211 enters shaft 1251 by passing through lumen 1213 and exit hole 1203. Mandrel 1250, with conduit 340 surrounding and shaft 1251 radially expanded (see, e.g., FIG. 12B), can then be inserted in fiber application device such as electrospinning unit 100 of FIG. 1.

Mandrel 1250 includes slot 1254 constructed and arranged to engage with rotational driving means, such as to rotate mandrel 1250 and conduit 340 in an electrospinning process. After a fiber matrix has been applied to conduit 340, shaft 1251 can be unexpanded (e.g. via a drying process, by applying a vacuum to connector 1211 and/or by otherwise reversing the expansion mechanisms such as by removing the expansion fluid), and mandrel 1250 removed from conduit 340.

As described in reference to FIG. 6 hereabove, the diameter of the applied fiber matrix can be adjusted by controlling the diameter of a mandrel shaft during the electrospinning process. For mandrel 1250 of FIGS. 12A and 12B, shaft 1251 diameter can be set (e.g. by adjusting the amount of swell of shaft 1251) to determine how and when restrictive forces are applied to conduit 340 by the fiber matrix as conduit 340 is expanded, such as when expanded by exposure to arterial blood pressure.

Figure 13A:
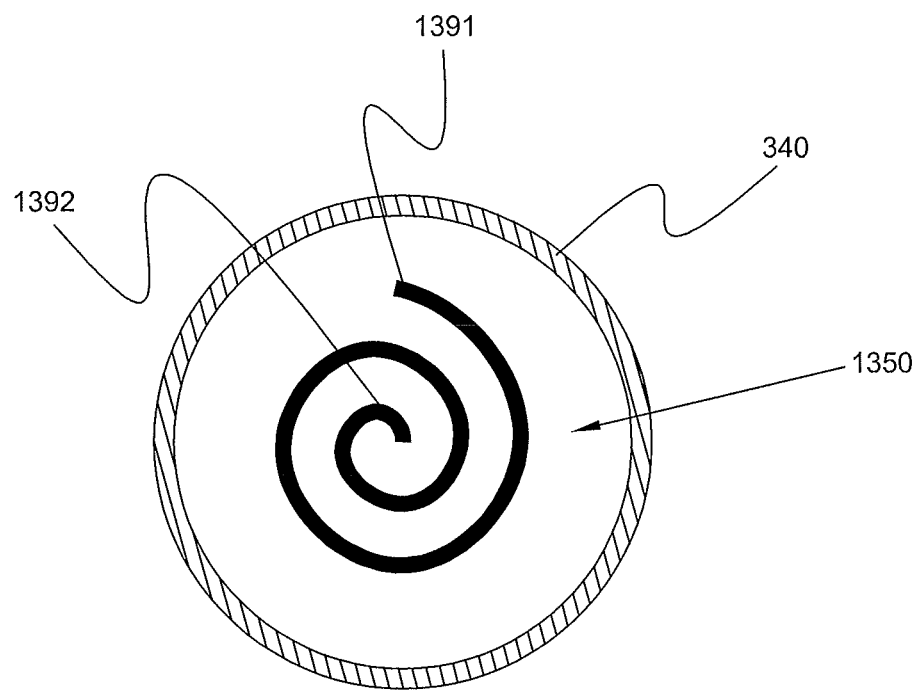
FIGS. 13A and 13B illustrate end views of an exemplary furlable mandrel inserted into a tubular member, in radially compressed and radially expanded states, respectively.
Figure 13B:
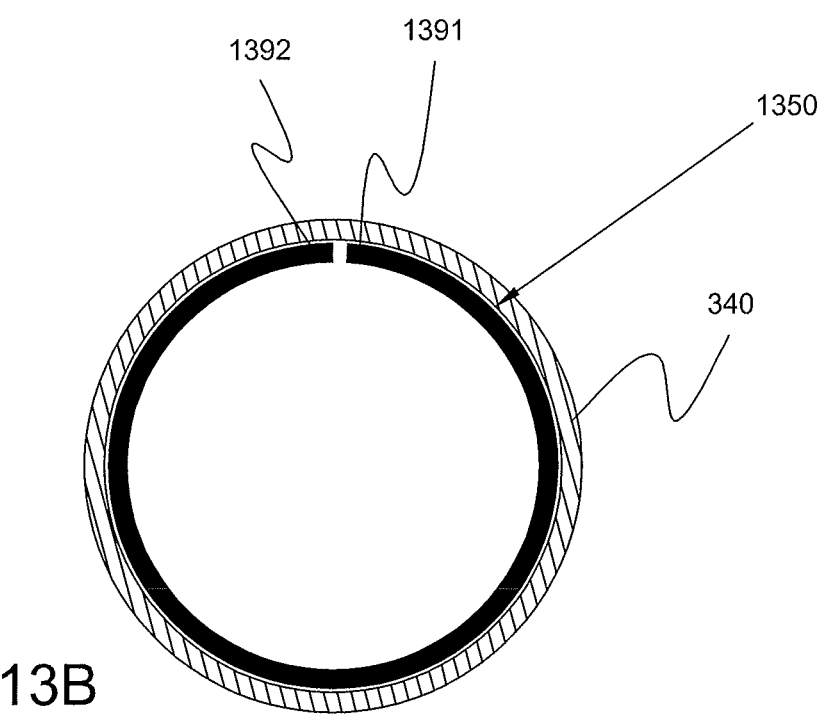

Referring now to FIGS. 13A and 13B, end views of a furlable mandrel inserted into a tubular member, in radially compressed and expanded states, respectively, are illustrated. Mandrel 1350 comprises a sheet of material, such as a sheet of metal such as Nitinol or stainless steel, which can be rolled or otherwise furled into a tubular structure. Mandrel 1350 comprises a first edge 1391 and a second edge 1392, and furling of mandrel 1350 causes mandrel 1350 to radially compress.

Referring specifically to FIG. 13A, mandrel 1350 has been furled into a radially compressed state, such that the diameter of mandrel 1350 is less than the inner diameter of conduit 340, allowing for atraumatic insertion of mandrel 1350 into conduit 340. After insertion, mandrel 1350 can unfurl, manually or without operator manipulation, such that the diameter of mandrel 1350 approximates the inner diameter of conduit 340 as is shown in FIG. 13B. Mandrel 1350 and conduit 340 can then be inserted into a fiber application unit to generate a graft device of the present invention. One or more end connectors, such as support 150a and/or 150b of FIG. 1, can be attached to the ends of mandrel 1350, not shown but typically configured to assist in the adjustment and/or locking of the furling condition of mandrel 1350.

As described in reference to FIG. 6 hereabove, the diameter of the applied fiber matrix can be adjusted by controlling the diameter of a mandrel shaft during the electrospinning process. For mandrel 1350 of FIGS. 13A and 13B, the diameter of mandrel 1350 can be set (e.g. by furling or unfurling) to determine how and when restrictive forces are applied to conduit 340 by the fiber matrix as conduit 340 is expanded, such as when expanded by exposure to arterial blood pressure.

Figure 14A:
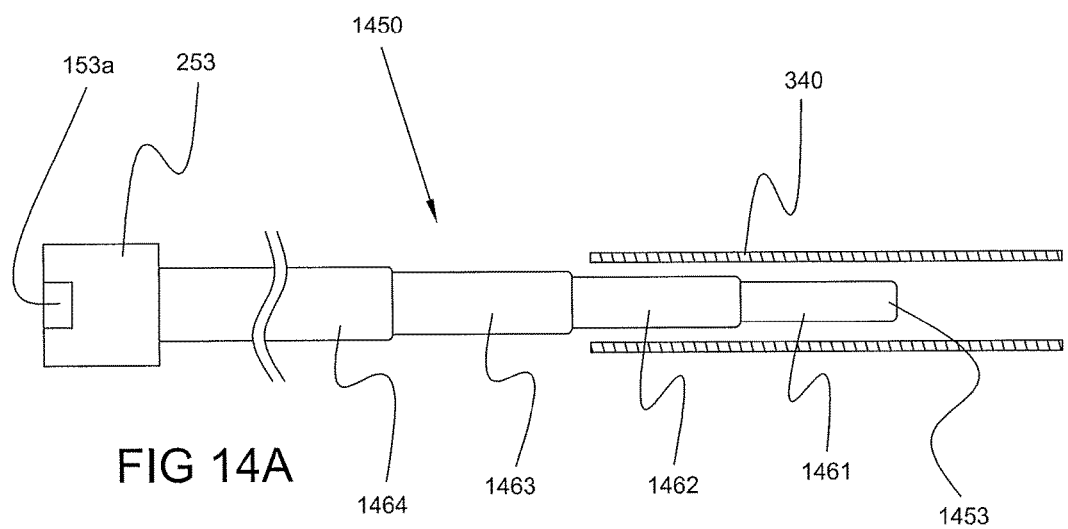
FIGS. 14A and 14B illustrate side sectional views of an exemplary telescopic mandrel, prior to and after insertion into a tubular member, respectively.
Figure 14B:
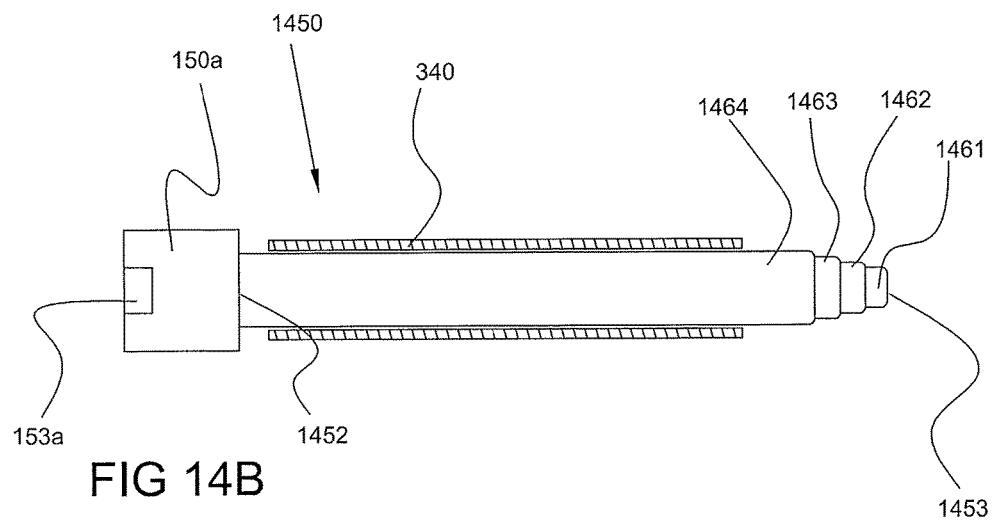

Referring now to FIGS. 14A and 14B, side sectional views of a telescopic mandrel, prior to and after insertion into a tubular member, respectively, are illustrated. Mandrel 1450 comprises a set of telescoping tubes, tubes 1461, 1462, 1463 and 1464, with tube 1461 slidingly received by tube 1462, tube 1462 slidingly received by tube 1463, and tube 1463 slidingly received by tube 1464.

Referring specifically to FIG. 14A, mandrel 1450 is shown in a state of full longitudinal elongation, such that end 1453 and smallest diameter tube 1461 can be atraumatically introduced into conduit 340.

In FIG. 14B, end 1453 has exited the distal end of conduit 340, tube 1464 has fully entered conduit 340, and mandrel 1450 has been placed in a fully retracted (i.e. longitudinally non-elongated) state. End 1452 of largest diameter tube 1464 is attached to support 150a which includes slot 153a configured to operably engage rotational drive means such as the shaft of a motor of an electrospinning unit.

The electrospinning chambers and/or cartridge housings of the present invention can assume numerous geometries, such as tubular housings, rectangular housings, and trapezoidal housings. The housings can include multiple portions, such as upper and lower portions, and can include components such as hinges, doors, slots and other openings. In one embodiment, the housing comprises a semi-rigid plastic pouch with an opening. Cartridges can include one or more sensors or transducers. In some embodiments, one or more nozzles are integral to the cartridge, such as at a side or bottom location to prevent gravitational dripping of any substance from the nozzle onto the conduit. Alternatively or additionally, one or more nozzles can be integral to the electrospinning unit of the apparatus of the present invention, similarly placed at any location into the cartridge, such as though a slot or door. While the conduit holder of the present invention has been described in detail as a rotatable mandrel, other conduit holders can be employed, rotating and fixed, such as to accommodate other forms of tissue such as nerve tissue, tendon tissue, muscle tissue, ligament tissue, organ and other non-linear tissues, and other tissues.

The mandrels of the present invention can assume numerous geometries, such as geometries which include one or more ends with a reduced diameter, a taper, a bevel, or rounded edge, or other atraumatic feature. The mandrels can be configured to be expanded, such as a radial expansion to a diameter less than, approximately equal to, or greater than a relaxed diameter of a vein graft or other tubular member of the present invention. The mandrels can be expanded along a majority of its length, or just a portion. One or more fluids can be delivered, along the full or partial length of the mandrel. Alternatively or additionally, one or more separate devices can be included, such as devices configured to assist in mandrel insertion or removal from a tubular member. Mandrels can include one or more coatings, such as a lubricious coating, along the full or partial length of the mandrel. Mandrels can include a lumen, such as a lumen configured to slidingly receive a shaft such as a guidewire shaft, and/or a lumen configured to deliver fluids. Mandrels can include an integral guidewire positioned at one or both ends, such as a guidewire comprising a J-tip configured for atraumatic insertion into a blood vessel of a patient.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth hereinbelow not be construed as being order-specific unless such order specificity is expressly stated in the claim.

What is claimed is:

1. A system for applying a fiber matrix on a tubular member, the system comprising:
    (a) a fiber matrix delivery assembly;
    (b) a tubular member; and
    (c) a mandrel comprising a porous portion, a mandrel first end and a mandrel second end,
        (i) wherein the mandrel is constructed and arranged to be atraumatically inserted into the tubular member, radially expanded within the tubular member, and attached to the fiber matrix delivery assembly, and
        (ii) wherein the mandrel comprises a braided construction, a helical construction, a guidewire attached to the mandrel first end, or any combination thereof.

2. The system of claim 1, wherein the mandrel further comprises a lumen.

3. The system of claim 1, wherein the system is constructed and arranged to deliver fluid from the porous portion of the mandrel to the tubular member.

4. The system of claim 1, wherein the mandrel comprises: a middle portion, and at least one of the mandrel first end or the mandrel second end comprises a smaller diameter than a diameter of the middle portion.

5. The system of claim 1, wherein the mandrel comprises a compressible tube constructed and arranged to radially expand when compressed.

6. The system of claim 1, wherein the mandrel is constructed and arranged to radially expand when exposed to a fluid.

7. The system of claim 1, wherein the mandrel comprises the guidewire attached to the mandrel first end, and wherein the guidewire is constructed and arranged to be removed from the mandrel first end.

8. The system of claim 1, wherein the system further comprises:
    a fluid delivery device operably attachable to at least one of the mandrel first end or the mandrel second end.

9. The system of claim 1, wherein the system further comprises:
    a rotational drive constructed and arranged to rotate the mandrel.

10. The system of claim 1, wherein the fiber matrix delivery assembly comprises an electrospinning unit.

11. The system of claim 1, wherein the tubular member comprises: living tissue selected from the group consisting of: vein, saphenous vein, artery, lymphatic duct, vas deferens, tear duct, intestine, esophagus, ureter, urethra, trachea, bronchi, duct tissue, Eustachian tube, fallopian tube, and combinations thereof.

12. The system of claim 1, wherein the tubular member comprises a saphenous vein.

13. The system of claim 1, wherein the tubular member comprises:
    an artificial conduit selected from the group consisting of: polytetrafluoroethylene (PTFE), expanded PTFE (ePTFE), polyvinylidene fluoride/hexafluoropropylene (PVDF-HFP), polyester, silicone, polyethylene, polypropylene, polyester-based polymer, polyether-based polymer, thermoplastic rubber, and combinations thereof.

14. The system of claim 1, wherein the porous portion of the mandrel comprises side holes.

15. The system of claim 14, wherein the side holes are equidistantly spaced.

* * * * *